(12) United States Patent
Ryu et al.

(10) Patent No.: US 7,783,352 B1
(45) Date of Patent: Aug. 24, 2010

(54) OPTIMIZING ANTI-TACHYCARDIA PACING FOR TERMINATING ATRIAL FIBRILLATION

(75) Inventors: Kyungmoo Ryu, Palmdale, CA (US); Jong Gill, Valencia, CA (US); Gene A. Bornzin, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 1062 days.

(21) Appl. No.: 11/473,403

(22) Filed: Jun. 23, 2006

(51) Int. Cl.
*A61N 1/08* (2006.01)
(52) U.S. Cl. .......................... 607/14; 607/15
(58) Field of Classification Search ............... 607/14, 607/15
See application file for complete search history.

(56) References Cited

U.S. PATENT DOCUMENTS

| | | | |
|---|---|---|---|
| 5,466,254 A | 11/1995 | Helland | 607/123 |
| 5,674,251 A | 10/1997 | Combs et al. | |
| 5,968,079 A | 10/1999 | Warman et al. | 607/5 |
| 6,654,639 B1 | 11/2003 | Lu | 607/17 |
| 7,295,873 B1* | 11/2007 | Min et al. | 607/14 |
| 2003/0050681 A1 | 3/2003 | Pianca et al. | 607/125 |
| 2003/0199932 A1 | 10/2003 | Struble | 607/14 |
| 2004/0220624 A1 | 11/2004 | Ritscher et al. | |
| 2004/0220630 A1 | 11/2004 | Mongeon et al. | 607/9 |
| 2005/0070965 A1* | 3/2005 | Kil et al. | 607/9 |
| 2005/0090869 A1 | 4/2005 | Sun et al. | 607/14 |
| 2007/0191894 A1* | 8/2007 | Li | 607/14 |

FOREIGN PATENT DOCUMENTS

WO   WO 2004/098707 A2   11/2004

OTHER PUBLICATIONS

NonFinal Office Action mailed Apr. 2, 2009; U.S. Appl. No. 11/473,715.
Final Office Action, mailed Nov. 17, 2009: Related U.S. Appl. No. 11/473,715.

* cited by examiner

*Primary Examiner*—Carl H. Layno
*Assistant Examiner*—Tammie K Heller

(57) ABSTRACT

An implantable system terminates atrial fibrillation by applying optimized anti-tachycardia pacing (ATP). In one implementation, the system senses and paces at multiple sites on the left atrium. At each site, the system senses reentrant circuits causing the atrial fibrillation. In one implementation, the system applies ATP tuned to the frequency of the reentrant circuit at the electrode that senses the most regular reentrant circuit. In another implementation, the system applies ATP at multiple electrodes, delivering each pulse at each site when the excitable gap is near the site. In other variations, the ATP is optimized for different patterns of sequential, simultaneous, or syncopated delivery to terminate the atrial fibrillation. The system can also monitor multiple heart chambers for cardiac events that favor terminating atrial fibrillation via ATP. The system then times delivery of the ATP according to these cardiac events.

8 Claims, 12 Drawing Sheets

ATRIAL FIBRILLATION THERAPY ENGINE 238

ATP INITIATION OPTIMIZER 302

MULTI-CHAMBER ANALYZER 308

PACING PARAMETERS OPTIMIZER 304

ATRIAL ATP OPTIMIZER 306

LEFT ATRIAL MULTI-ELECTRODE MANAGER 310

Fig. 3

ANTERIOR VIEW

1000

```
┌─────────────────────────────────────────┐
│   SENSE AND PACE AT MULTIPLE SITES      │
│     OF A LEFT ATRIUM OF A HEART         │
│                 1002                    │
└─────────────────────────────────────────┘
```

```
┌─────────────────────────────────────────┐
│  SENSE REENTRANT CIRCUITS IN THE LEFT   │
│  ATRIUM, THE REENTRANT CIRCUITS         │
│  CAUSING ATRIAL FIBRILLATION            │
│                 1004                    │
└─────────────────────────────────────────┘
```

```
┌─────────────────────────────────────────┐
│  DELIVER ATP AT ONE OR MORE OF THE      │
│  MULTIPLE SITES TO TERMINATE THE        │
│  ATRIAL FIBRILLATION, TIMED AT EACH     │
│  SITE TO A CYCLE DURATION OF AT LEAST   │
│  ONE OF THE REENTRANT CIRCUITS          │
│                 1006                    │
└─────────────────────────────────────────┘
```

*Fig. 10*

OPTIMIZING ANTI-TACHYCARDIA PACING FOR TERMINATING ATRIAL FIBRILLATION

CROSS REFERENCE TO RELATED APPLICATIONS

The application is related to co-pending U.S. patent application Ser. No. 11/473,715, filed Jun. 23, 2006, titled "Optimizing Anti-Tachycardia Pacing For Terminating Atrial Fibrillation."

FIELD OF THE INVENTION

Subject matter presented herein relates generally to implantable medical devices and more particularly to optimizing anti-tachycardia pacing for terminating atrial fibrillation.

BACKGROUND

Anti-tachycardia Pacing (ATP) has been used to convert ventricular tachycardias into normal sinus rhythm, but cannot always be relied upon to return the heart to normal sinus rhythm. Nonetheless, ATP is a standard treatment option to terminate most reentrant tachycardias. Also, ATP treatment has demonstrated high efficacy in terminating atrial flutter, however, it is very ineffective in terminating atrial fibrillation.

Atrial Fibrillation Arrhythmia

Atrial fibrillation (also referred to as "AF" or "afib") is an abnormal heart rhythma—cardiac arrhythmia—of the two upper chambers of the heart. Heartbeats are normally initiated after electricity generated in the right atrium by the sinoatrial (SA) node spreads in an orderly manner over and through the heart to cause coordinated contraction of heart muscle and thus, pumping of blood. In atrial fibrillation, the regular electrical impulses of the sinoatrial node are replaced by disorganized, rapid electrical impulses that may result in irregular heartbeats.

Atrial fibrillation is one of the most common cardiac arrhythmias, but fortunately it is not as immediately serious as ventricular tachycardia. The risk of developing atrial fibrillation increases with age—atrial fibrillation affects four percent of individuals in their 80s. An individual may spontaneously alternate between atrial fibrillation and a normal rhythm (this is known as paroxysmal atrial fibrillation) or may continue with atrial fibrillation as the dominant cardiac rhythm without reversion to the normal rhythm (this is known as chronic atrial fibrillation). Atrial fibrillation is often asymptomatic, but may result in symptoms of palpitations, fainting, chest pain, or even heart failure. These symptoms are especially common when atrial fibrillation results in a heart rate that is either too fast or too slow. In addition, the erratic motion of the atria leads to blood stasis, especially in the atrial appendages, which predisposes to blood clots that may migrate from the heart to the brain and other organs. Thus, atrial fibrillation is an important risk factor for stroke, the most feared complication of atrial fibrillation.

Sometimes the symptoms of atrial fibrillation are treated with medications that slow the heart rate. Several medications as well as electrical cardioversion may be used to convert atrial fibrillation to a normal heart rhythm. Surgical and catheter-based therapies may also be used to prevent atrial fibrillation in certain individuals. Typically, patients with atrial fibrillation are given blood thinners such as warfarin to protect them from strokes.

Atrial fibrillation may be diagnosed on an electrocardiogram, in which characteristic findings (e.g., lead II of a rhythm strip) are: absence of P waves, unorganized electrical activity in place of the missing P waves, and irregularity of the R-R intervals due to irregular conduction of impulses to the ventricles. Holter monitoring (continuous ECG recording for 24 hours or longer) may be used to detect episodes of paroxysmal atrial fibrillation.

Pathophysiology of Atrial Fibrillation

The normal electrical conduction system of the heart allows an original impulse generated by the SA node to be propagated, stimulating the myocardium to contract as the impulse propagates from the SA node. The speed of the propagating electrical wave through various cardiac tissues and conduction bundles and the distance of the relative parts of the heart from the SA node or from a conductive bundle determine a sequential order according to which the different compartments of the heart are stimulated to contract. This ordered sequential contraction of the different parts of the heart causes efficient pumping. If the timing is off, then the pumping suffers or stops.

In atrial fibrillation, the regular impulses produced by the SA node to provide rhythmic contraction of the heart are overwhelmed by rapid randomly generated electrical discharges, e.g., as produced by larger areas of atrial tissue. Atrial fibrillation can be distinguished from atrial flutter, which is a more organized electrical circuit, usually in the right atrium, which produces characteristic saw toothed waves on an electrocardiogram.

In particular, atrial fibrillation can be caused and maintained by one or more "reentrant circuits" that produce the undesirable fibrillatory conduction. A reentrant circuit is typically a physical and electrical feedback loop composed of cardiac cells that repeatedly cycle electrical impulses in a tight circle and spin off abnormal impulses that propagate over the heart causing the disruption characteristic of atrial fibrillation. Such a problem feedback loop may be originated by a trigger, such as an abnormally occurring spontaneous depolarization of cell membrane in the myocardial tissue. Some reentrant circuits may come and go, may become chaotic for a few seconds, and then return, etc. However, most of these sources of atrial activation tend to be regular, and very consistent, or else atrial fibrillation would break of its own accord. A typical cycle duration for such a reentrant circuit is on the order of 100-200 milliseconds (ms). This is the equivalent of 600 beats per minute at a 100 ms cycle duration. If there is no such trigger and no resulting reentrant circuit, then fibrillatory conduction will not be there, i.e., the electrical conduction will be normal intrinsic conduction from an intrinsic rhythm (e.g., normal sinus rhythm).

Reentrant circuits can be further understood in terms of cellular action potentials continually propagating around the reentrant circuit at a rate considerably faster than the heart's intrinsic rate, provided that the reentrant wave front, i.e. the head of the propagation wave front, moves slowly enough that tissue ahead recovers excitability, i.e., slowly enough that a tail (or end of the propagation wave front) can form. The spatial extent of unexcitable tissue in this circuit is termed the reentrant wavelength, and is approximated by the product of the head's velocity and the action potential duration. As long as the wavelength is less than the circuit's perimeter, i.e. the reentrant path length, the head and tail remain separated by an excitable gap (of tissue waiting to be stimulated). Termination of anatomic reentry requires elimination of the excitable gap, which can be achieved by appropriate pacing. An appropriately timed stimulus (i.e., a pacing pulse) will initiate action potentials that propagate in both directions, colliding with the head and "blocking in" the tail.

In more simplified terms, the reentrant circuit can be thought of as a conduction wave front propagating along a tissue mass of somewhat circular geometry. This circular conduction will consist of a portion of refractory tissue and a portion of excitable tissue. To terminate the circuit, a pacing stimulus should be provided at the time and location when the tissue just comes out of refractoriness. If this occurs, the paced stimulation wave front proceeds toward the advancing wave front of the circuit, colliding with the wave front and interrupting the circuit. If the pacing stimulus (i.e., pacing pulse) arrives too soon it will be ineffective because the tissue will still be in refractoriness. If the stimulus arrives too late, it will generate wave fronts both towards the advancing wave front and towards the tail of the circuit. Although one pacing-generated wave front will collide with the advancing wave front of the reentrant circuit and will halt is progress, the latter pacing-generated wave front will act to sustain the reentrant circuit.

Conventional Treatments for Atrial Fibrillation

The main goals of treatment for atrial fibrillation are to prevent temporary circulatory instability and to prevent stroke. Rate and rhythm control are principally used to achieve the former, while anticoagulation may be required to decrease the risk of the latter. Rate control treatments aim to restore a normal heart rate, usually 60 to 100 beats per minute. Rhythm control seeks to restore the heart's normal rhythm, referred to as "normal sinus rhythm." Rate control medications may include beta-blockers, calcium channel blockers and cardiac glycosides. These medications aim to slow down the impulses emanating from the atria and to slow down conduction of these impulses to the ventricles. Rhythm control techniques include electrical and chemical cardioversion. Electrical cardioversion applies a DC electrical shock to restore normal sinus rhythm. Chemical cardioversion relies on medications, such as amiodarone, propafenone, or flecainide, which make the heart tissue less excitable. These medications are sometimes used together with electrical cardioversion. Cardioversion poses the risk of systemic embolization by a blood clot from a location of previously stagnating blood, such as the previously fibrillating left atrium. Thus, cardioversion may require adequate anticoagulation in patients who have been in atrial fibrillation for more than a day or two.

When rate control medications are ineffective and normal sinus rhythm cannot be restored via cardioversion, then sometimes rate control is attempted by "ablation," that is, destroying cardiac tissue responsible for the abnormal impulse production. In one alternative, this solution attempts to destroy the atrioventricular (AV) node—the group of cells electrically connecting the upper and lower chambers of the heart and serving as a re-transmitter of the SA node's original impulse. Electrical stimulation by an implanted cardiac device is substituted in its place.

In another variation of ablation, a technique tries to destroy groups of cells near the pulmonary arteries where atrial fibrillation is thought to originate. Or again, another technique tries to ablate relatively large areas of atrial tissue in an attempt to block atrial fibrillation from spontaneously arising. There are several other variations of the ablation technique. Radiofrequency ablation aims to destroy abnormal electrical pathways in the cardiac tissue—using RF energy. A radiofrequency emitting electrode is placed into the heart to destroy the tissue thought to be responsible for the abnormal electrical activity. Cryoablation freezes tissue to kill cardiac cells using a coolant that flows through a catheter. Microwave ablation does the same, but by heating the tissue to be destroyed. Such ablation techniques have gained popularity for atrial fibrillation that does not respond to the more conventional medication and cardioversion treatments.

The abnormal electrophysiology of atrial fibrillation can also be modified by surgically destroying cardiac tissue, and such procedures, such as the Cox maze procedure, are commonly performed concomitantly with cardiac surgery. More recently, minimally invasive surgical variations on the Cox Maze procedure ("minimaze" procedures) have also been developed.

The Cox maze procedure is an open-heart surgical procedure intended to eliminate atrial fibrillation, in which a series of incisions are made in the atria, the incisions made in a maze-like pattern. The intention is to eliminate atrial fibrillation by blocking potentially disruptive electrical circuits with non-conductive scar tissue. The Cox maze procedure is involved, using an extensive series of incisions inside of the heart, incisions through both atria, a vertical incision through the breastbone, and cardiopulmonary bypass (i.e., a heart-lung machine during the operation). Improved versions of the Cox maze procedure are now the state-of-the-art surgical treatment for atrial fibrillation "Minimaze" techniques are miniature versions of the original maze procedure, and usually less invasive than the Cox maze procedure, not requiring a vertical incision in the breastbone or cardiopulmonary bypass. These procedures may use the aforementioned microwave, radiofrequency, or even acoustic energy to ablate atrial tissue near the pulmonary veins.

There are problems with these ablation techniques, even though many are favored as the state-of-the-art solution for atrial fibrillation. Clinicians typically ablate by performing a left side ablation, boring a hole through the atrial septum from right to left. The patient continues on anticoagulation therapy. The boring of a hole damages the heart itself, even though the damaged tissue may interrupt an abnormal conduction system and cure atrial fibrillation, at least temporarily. But such procedures can damage the heart (atrium) so much that it cannot contract effectively. Moreover, long-term efficacy of ablation has not been proven yet. The efficacy of AF ablation is thought to be around 60-85%, some even conjecture 90% efficacy. Atrial fibrillation can recur anytime, however. Thus, two undesirable consequences of ablation therapy include frequent reoccurrences and impairment of the mechanical action of the atria. Such may lead to stagnating blood in the atria—a silent recurrence that may give rise to stroke, the same feared complication of atrial fibrillation that the ablation technique sought to relieve.

SUMMARY

An implantable system terminates atrial fibrillation by applying optimized anti-tachycardia pacing (ATP). In one implementation, the system senses and paces at multiple sites on the left atrium of the heart. At each site, the system tries to sense reentrant circuits causing the atrial fibrillation. In one implementation, the system applies ATP that is tuned to the frequency of the reentrant circuit via one electrode at a time on the left atrium, beginning with the electrode that senses the most regular reentrant circuit. In another implementation, the system applies ATP at multiple electrodes by delivering each pulse at a different time at each site, depending on when the excitable gap of a reentrant circuit is near the particular site. In other variations, the ATP is optimized for different patterns of sequential, simultaneous, or syncopated delivery to terminate the atrial fibrillation. The system can also monitor multiple heart chambers for certain cardiac events that provide favorable opportunities for terminating atrial fibrillation via ATP. The system then times delivery of the ATP according to these cardiac events.

BRIEF DESCRIPTION OF THE DRAWINGS

FIG. 3 is a block diagram of an exemplary atrial fibrillation therapy engine.

FIG. 10 is a flow diagram of a first exemplary method of treating atrial fibrillation using ATP.

DETAILED DESCRIPTION

Overview

Figure 1:
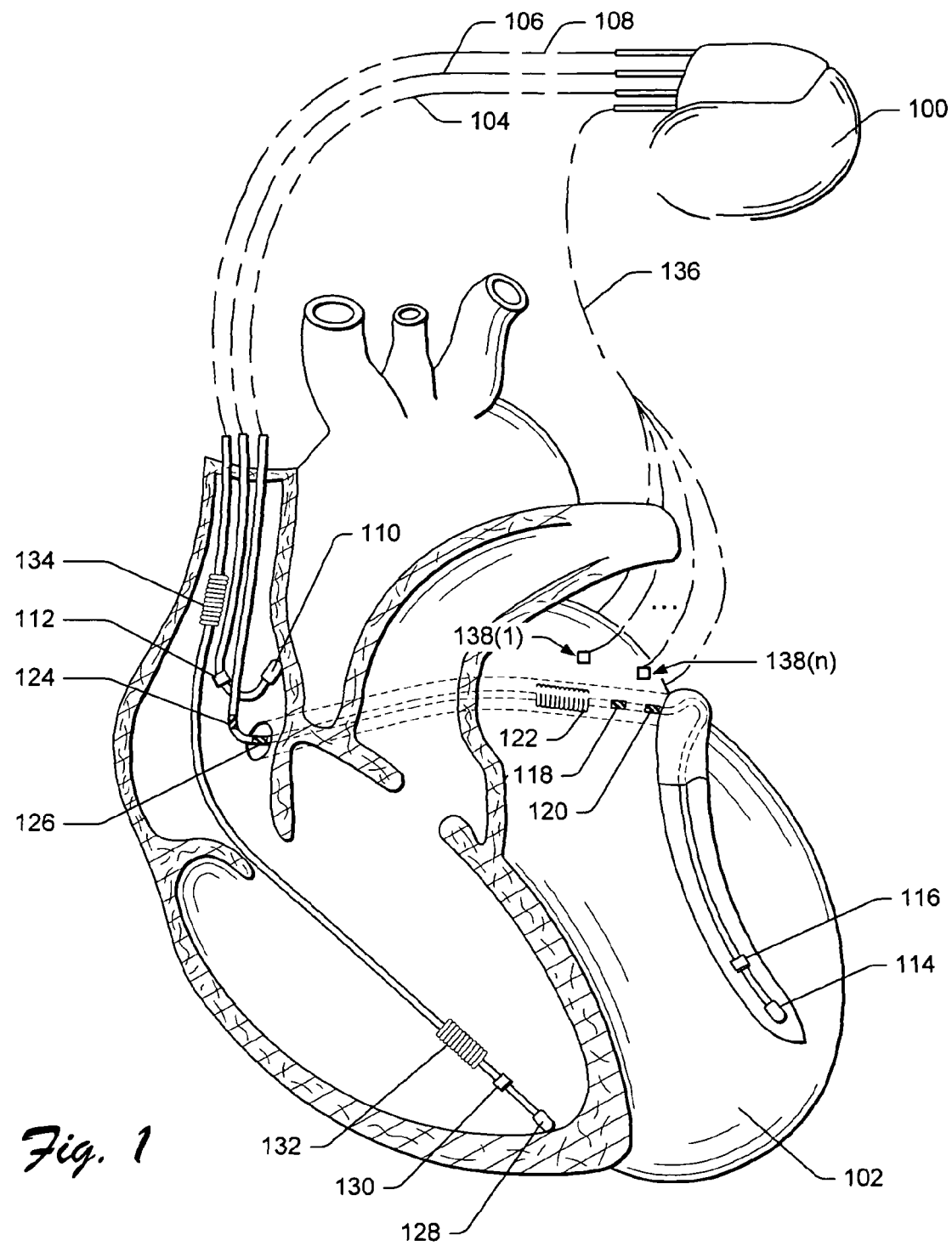
FIG. 1 is a diagram of an exemplary stimulation device in relation to a human heart.

This disclosure describes systems and methods for optimizing anti-tachycardia pacing (ATP) to treat atrial fibrillation (AF) and other arrhythmias, such as atrial flutter. In one implementation, an exemplary system monitors various cardiac events—electrical and hemodynamic changes—that are favorable events for timing and optimizing ATP parameters so that ATP can be effective in terminating atrial fibrillation. For example, the system may analyze hemodynamics and electrical waveform morphology in multiple heart chambers to find a sudden change in a hemodynamic parameter, and use this landmark as a precise timing point for initiating ATP to terminate the atrial fibrillation. This first type of optimization, moreover, has general applicability to treating many types of arrhythmias (and is not limited to atrial just arrhythmias).

In a second type of optimization, the system analyzes input from multiple electrodes disposed epicardially on or near the left atrium, particularly around the left pulmonary veins and Bachmann bundle areas. The system monitors for regularly cycling reentrant circuits and then uses this input to optimize ATP for terminating atrial fibrillation via the same multiple electrodes. These electrodes can be placed on and/or in the left atrium, for example, by pericardial access during an implantation procedure. The system uses the multiple electrodes to sense abnormal activation on the left atrium and the abnormal electrical pathways in cardiac tissue that drive atrial fibrillation. At each electrode, the system senses the cycle duration of reentrant circuits, if any, that are detectable at each electrode. ATP pacing parameters are then optimized using this information as an effective treatment for terminating atrial fibrillation.

Specifically, the system can sense, at each electrode, the regular arrival of an excitable gap being propagated as part of a reentrant circuit, and then can synchronize ATP at each electrode with the timing of the recurring presence or proximity of the excitable gap.

There are several other ways that the ATP can be applied over the multiple electrodes on the left atrium. In one implementation, each pulse of ATP that is being applied at a given pacing rate is applied at different times at each electrode in a syncopated manner in order to match the passage of the excitable gap at each particular electrode. In another implementation, each electrode applies ATP at a different pacing rate to match the cycle durations of different reentrant circuits operative near each electrode. In yet another implementation, the ATP is only applied at one electrode at a time, beginning at the electrode at which the most stable and regular atrial activation is sensed. If the atrial fibrillation persists, then ATP is applied at the electrode at which the second-most stable and regular atrial activation was sensed. In yet another implementation, ATP is applied simultaneously at all electrodes on the left atrium in an attempt to resynchronize the electrical conduction of the left atrium. Relatively high voltages may be used in these implementations, especially the latter, to terminate the atrial fibrillation.

In some of the implementations just described, the probability of ATP succeeding in terminating atrial fibrillation is related to the ability of each pacing stimulation wave front to arrive at the location of a targeted reentrant circuit in such a manner that the reentrant circuit is modified or interrupted. Factors influencing this process may include the distance of the pacing electrode(s) from the reentrant circuit, the pacing stimulus energy, and the timing of the pacing stimuli relative to the conduction velocities and refractory periods of the myocardium. Thus, there are many parameters that can be optimized to make ATP suitable for effectively terminating atrial fibrillation. The exemplary system achieves the ability to apply ATP sequentially, simultaneously, or in a syncopated manner at multiple electrodes on the left atrium, having the advantage that the ATP at each electrode can be synchronized with the propagating excitable gap to achieve optimal termination of reentrant circuits.

Exemplary Stimulation Device

Before describing the optimization of ATP and its parameters for terminating atrial fibrillation, an example device in which optimized ATP can be computed based on sensed input and in which optimized ATP parameters can be delivered therapeutically is now described. As shown in FIG. 1, a stimulation device 100 is in electrical communication with a patient's heart 102 by way of four leads, 104, 106, 108, and 136 for delivering multi-chamber stimulation, anti-tachycardia pacing, and shock therapy, etc. Not every configuration has all of the illustrated electrodes, but a real configuration may include some of the illustrated electrodes and/or even more electrodes than illustrated.

To sense atrial cardiac signals and to provide right atrial chamber stimulation therapy, the stimulation device 100 is coupled to an implantable right atrial lead 106, typically having an atrial tip electrode 110 and an atrial ring electrode 112, which typically is implanted in the patient's right atrial appendage. Stimulation device 100 is also known as and referred to as a pacing device, a pacing apparatus, a cardiac rhythm management device, or an implantable cardiac stimulation device. Stimulation device 100 can be an implantable cardioverter/defibrillator (ICD).

To sense left atrial and ventricular cardiac signals and to provide left chamber pacing therapy, the stimulation device 100 is coupled to a "coronary sinus" lead 104 designed for placement in the "coronary sinus region" via the coronary sinus opening for positioning a distal electrode adjacent to the left ventricle or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 104 is designed to receive atrial and ventricular cardiac signals and to deliver left ventricular pacing therapy using a left ventricular (LV) tip electrode 114 and a LV ring electrode 116. Left atrial pacing therapy uses, for example, first and second left atrial (LA) ring electrodes 118 and 120. Shocking therapy can be performed using at least a left atrial (LA) coil electrode 122. For a description of an exemplary coronary sinus lead, see U.S. Pre-Grant Publication No. 2003/0050681, "A Self-Anchoring Coronary Sinus Lead" (Pianca et al.), and U.S. Pat. No. 5,466,254 to Helland, entitled, "Coronary Sinus Lead with Atrial Sensing Capability," which patent documents are incorporated herein by reference. Coronary sinus lead 104 may also include a pair of right atrial (RA) ring electrodes 124 and 126, which may be used to provide right atrial chamber pacing therapy.

The stimulation device 100 is also shown in electrical communication with the patient's heart 102 by way of an implantable right ventricular lead 108, typically having an right ventricular (RV) tip electrode 128, an RV ring electrode 130, an RV coil electrode 132, and a superior vena cava (SVC) coil electrode 134 (also known as a right atrial (RA) coil electrode). Typically, the right ventricular lead 108 is transvenously inserted into the heart 102 so as to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of receiving cardiac signals, and delivering stimulation in the form of pacing and shock therapy to the right ventricle.

An implantable left atrium lead 136 couples the stimulation device 100 to multiple electrodes, such as 138(1), which have been placed on, in, or epicardially around the left atrium. The multiple electrodes placed on the left atrium may be as few as two or as many as twelve or more. These left atrial electrodes may be unipolar or bipolar type electrodes. Placement of the left atrial electrodes, such as electrode 138(1), may be made during implantation by making an incision in the pericardial sac and placing the electrodes surgically.

Figure 2:
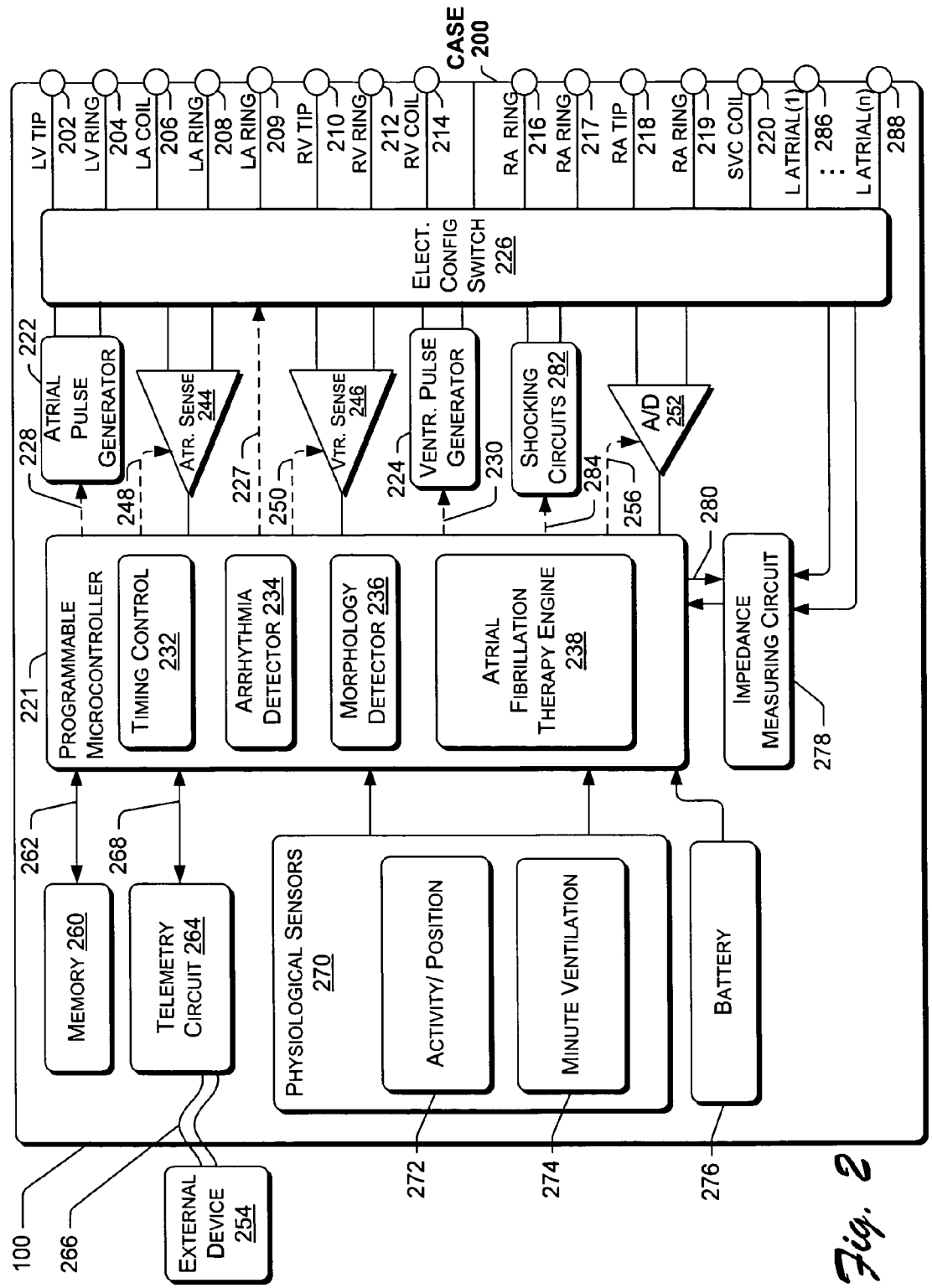
FIG. 2 is a block diagram of components of the exemplary stimulation device of FIG. 1.

FIG. 2 shows an exemplary block diagram depicting various components of the exemplary stimulation device 100. The components are typically contained in a case 200, which is often referred to as the "can", "housing", "encasing", or "case electrode", and may be programmably selected to act as the return electrode for unipolar operational modes. The case 200 may further be used as a return electrode alone or in combination with one or more of the coil electrodes 122, 132, 134 for stimulating purposes. The case 200 further includes a connector (not shown) having a plurality of terminals (202, 204, 206, 208, 209, 210, 212, 214, 216, 217, 218, 219, and 220—shown schematically with the names of the electrodes to which they are connected shown next to the terminals), including:

a left ventricular tip terminal (LV TIP) 202 for left ventricular tip electrode 114;

a left ventricular ring terminal (LV RING) 204 for left ventricular ring electrode 116;

a left atrial shocking terminal (LA COIL) 206 for left atrial coil electrode 122;

a left atrial ring terminal (LA RING) 208 for left atrial ring electrode 118;

a left atrial ring terminal (LA RING) 209 for left atrial ring electrode 120;

a right ventricular tip terminal (RV TIP) 210 for right ventricular tip electrode 128;

a right ventricular ring terminal (RV RING) 212 for right ventricular ring electrode 130;

a right ventricular shocking terminal (RV COIL) 214 for RV coil electrode 132;

a right atrial ring terminal (RA RING) 216 for atrial ring electrode 124;

a right atrial ring terminal (RA RING) 217 for right atrial ring electrode 126;

a right atrial tip terminal (RA TIP) 218 for atrial tip electrode 110;

a right atrial ring terminal (RA RING) 219 for atrial ring electrode 112;

a SVC shocking terminal (SVC COIL) 220 for right atrial SVC coil electrode 134;

a left atrial pacing terminal (L. Atrial(1)) 286 for epicardial left atrial electrode 138(1); and additional left atrial pacing terminals (L. Atrial(n)) 288 for additional left atrial electrodes 138(n) placed in, around, or epicardially on the left atrium.

An exemplary stimulation device 100 may include a programmable microcontroller 221 that controls various operations of the stimulation device 100, including cardiovascular monitoring, hemodynamic monitoring, and cardiovascular stimulation therapy. Microcontroller 221 includes a microprocessor (or equivalent control circuitry), RAM and/or ROM memory, logic and timing circuitry, state machine circuitry, and I/O circuitry.

The exemplary stimulation device 100 may further include an atrial pulse generator 222 and a ventricular pulse generator 224 that generate pacing stimulation pulses for delivery by the right atrial lead 106, the coronary sinus lead 104, and/or the right ventricular lead 108 via an electrode configuration switch 226. The electrode configuration switch 226 may include multiple switches for connecting the desired electrodes to the appropriate I/O circuits, thereby providing complete electrode programmability. Accordingly, switch 226, in response to a control signal 227 from the microcontroller 221, determines the polarity of the stimulation pulses (e.g., unipolar, bipolar, etc.) by selectively closing the appropriate combination of switches.

To provide stimulation therapy in each of the four chambers of the heart, the atrial and ventricular pulse generators 222 and 224 may include dedicated, independent pulse generators, multiplexed pulse generators, or shared pulse generators. The pulse generators 222 and 224 are controlled by the microcontroller 221 via appropriate control signals 228 and 230, respectively, to trigger or inhibit the stimulation pulses.

Microcontroller 221 is illustrated as including timing control circuitry 232 to control the timing of the stimulation pulses (e.g., pacing rate, atrioventricular (AV) delay, atrial interconduction (A-A) delay, or ventricular interconduction (V-V) delay, native atrial event to native or stimulated ventricular event (PV) delay, (AV/PV) delay, etc.). The timing control circuitry may also be used for the timing of refractory periods, blanking intervals, noise detection windows, evoked response windows, alert intervals, marker channel timing, and so on.

Microcontroller 221 may also implement an arrhythmia detector 234, a morphology detector 236, and an atrial fibrillation therapy engine 238. The microcontroller 221 may process input from physiological sensors 270, such as accelerometers of an activity/position module 272, and a minute ventilation module 274 etc., The components 234, 236 and 238 may be implemented in hardware as part of the microcontroller 221, or as software/firmware instructions programmed into an implementation of the stimulation device 100 and executed on the microcontroller 221 during certain modes of operation. Although not shown, the microcontroller 221 may further include other dedicated circuitry and/or firmware/software components that assist in monitoring various conditions of the patient's heart and managing pacing therapies.

Atrial sensing circuits 244 and ventricular sensing circuits 246 may also be selectively coupled to the right atrial lead 106, coronary sinus lead 104, and the right ventricular lead 108, through the switch 226 to detect the presence of cardiac activity in each of the four chambers of the heart. The sensing circuits 244 and 246 may include dedicated sense amplifiers, multiplexed amplifiers, or shared amplifiers. Switch 226 determines the "sensing polarity" of the cardiac signal by selectively closing the appropriate switches. In this way, the clinician may program the sensing polarity independent of the stimulation polarity.

Each sensing circuit 244 and 246 may employ one or more low power precision amplifiers with programmable gain and/or automatic gain control, bandpass filtering, and a threshold detection circuit to selectively sense the cardiac signal of interest. The automatic gain control enables the exemplary stimulation device 100 to sense low amplitude signal characteristics of atrial or ventricular fibrillation.

The outputs of the atrial and ventricular sensing circuits 244 and 246 are connected to the microcontroller 221 which, in turn, is able to trigger or inhibit the atrial and ventricular pulse generators 222 and 224 in a demand fashion in response to the absence or presence of cardiac activity in the appropriate chambers of the heart. The sensing circuits 244 and 246 receive control signals from the microcontroller 221 over signal lines 248 and 250 to control, for example, the gain and/or threshold of polarization charge removal circuitry (not shown) and the timing of blocking circuitry (not shown) optionally coupled to the inputs of the sensing circuits 244, 246.

Cardiac signals are supplied to an analog-to-digital (A/D) data acquisition system 252, which is configured to acquire intracardiac electrogram signals, convert the raw analog data into a digital signal, and store the digital signals for later processing and/or telemetric transmission to an external device 254. The data acquisition system 252 is coupled to the right atrial lead 106, the coronary sinus lead 104, and the right ventricular lead 108 through the switch 226 to sample cardiac signals across any pair of desired electrodes.

The data acquisition system 252 is coupled to the microcontroller 221, or other detection circuitry, to assist in detecting an evoked response from the heart 102 in response to an applied stimulus, which is often referred to as detecting "capture". Capture occurs when an electrical stimulus applied to the heart is of sufficient energy to depolarize the cardiac tissue, thereby causing the heart muscle to contract. The microcontroller 221 detects a depolarization signal during a window following a stimulation pulse, the presence of which indicates that capture has occurred. The microcontroller 221 enables capture detection by triggering the ventricular pulse generator 224 to generate a stimulation pulse, starting a capture detection window using the timing control circuitry 232 within the microcontroller 221, and enabling the data acquisition system 252 via control signal 256 to sample the cardiac signal that falls in the capture detection window and, based on the amplitude, determines if capture has occurred.

The microcontroller 221 is further coupled to a memory 260 by a suitable data/address bus 262. The programmable operating parameters used by the microcontroller 221 are stored in memory 260 and used to customize the operation of the exemplary stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, wave shape and vector of each shocking pulse to be delivered to the patient's heart 102 within each respective tier of therapy.

The operating parameters of the exemplary stimulation device 100 may be non-invasively programmed into the memory 260 through a telemetry circuit 264 in telemetric communication via communication link 266 with the external device 254, such as a programmer, local transceiver, or a diagnostic system analyzer. The microcontroller 221 can activate the telemetry circuit 264 with a control signal 268. The telemetry circuit 264 allows intracardiac electrograms and status information relating to the operation of the exemplary stimulation device 100 (as contained in the microcontroller 221 or memory 260) to be sent to the external device 254 through an established communication link 266.

The physiological sensors 270 referred to above can further include, for example, "rate-responsive" sensors that adjust pacing stimulation rates according to the exercise state of the patient. Accordingly, the microcontroller 221 responds by adjusting the various pacing parameters (such as rate, AV Delay, V-V Delay, etc.) at which the atrial and ventricular pulse generators 222 and 224 generate stimulation pulses.

The physiological sensors 270 may include mechanisms and sensors to detect bodily movement (272), minute ventilation 274, changes in blood pressure, changes in cardiac output, changes in the physiological condition of the heart, diurnal changes in activity (e.g., detecting sleep and wake states), G-force acceleration of the ICD case 200, duration of the cardiac QT interval, blood oxygen saturation, blood pH, changes in temperature, respiration rate, and QRS wave duration. While shown as being included within the exemplary stimulation device 100, the physiological sensor(s) 270 may also be external to the exemplary stimulation device 100, yet still be implanted within or carried by the patient, e.g., a blood pressure probe. Examples of physiological sensors external to the case 200 that may be deployed by stimulation device 100 include sensors that, for example, sense respiration activities, $O_2$ saturation, evoked response, pH of blood, and so forth.

The illustrated physiological sensors 270 include one or more activity/position sensors 272 (e.g., 1D or 3D accelerometers, movement sensors, etc.) to detect changes in the patient's position. The activity/position sensors 272 can be used to assist detection of orthostatic hypotension caused by transition from a less upright posture to a comparatively more upright posture. One example postural change leading to orthostatic hypotension in susceptible individuals is a movement from a supine position in a rest state (e.g., sleeping in bed) to an upright position in a non-rest state (e.g., sitting or standing up).

In one configuration, accelerometer output signal is band-pass-filtered, rectified, and integrated at regular timed intervals. A processed accelerometer signal can be used as a raw activity signal. The device derives an activity measurement based on the raw activity signal at intervals timed according to the cardiac cycle. The activity signal alone can be used to indicate whether a patient is active or resting. The activity measurement can further be used to determine an activity variance parameter. A large activity variance signal is indicative of a prolonged exercise state. Low activity and activity variance signals are indicative of a prolonged resting or inactivity state.

The minute ventilation (MV) sensor 274 may also be included in the physiological sensors 270 in order to sense rate and depth of breathing. Minute ventilation can be measured as the total volume of air that moves in and out of a patient's lungs in a minute. The MV sensor 274 may use an impedance measuring circuit 278 to sense air movement by measuring impedance across the chest cavity.

The impedance measuring circuit 278 is enabled by the microcontroller 221 via a control signal 280 and can be used for many things besides the abovementioned detection of air movement in and out of the lungs, including: lead impedance surveillance during acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring cardiac stroke volume; detecting the opening of heart valves; and so forth. The impedance measuring circuit 278 may be coupled to the switch 226 so that any desired electrode may be used.

The exemplary stimulation device 100 additionally includes a battery 276 that provides operating power to all of the components shown in FIG. 2. The battery 276 is capable of operating at low current drains for long periods of time (e.g., less than 10 µA), and is capable of providing high-current pulses (for capacitor charging) when the patient requires a shock pulse (e.g., in excess of 2 A, at voltages above 2 V, for periods of 10 seconds or more). The battery 276 also desirably has predictable discharge characteristics so that elective replacement time can be detected. As one example, the exemplary stimulation device 100 employs lithium/silver vanadium oxide batteries.

The exemplary stimulation device 100 can further include magnet detection circuitry (not shown), coupled to the microcontroller 221, to detect when a magnet is placed over the exemplary stimulation device 100. A magnet may be used by a clinician to perform various test functions of the exemplary stimulation device 100 and/or to signal the microcontroller 221 that an external programmer (e.g., 254) is in place to receive or transmit data to the microcontroller 221 through the telemetry circuits 264.

The microcontroller 221 further controls a shocking circuit 282 via a control signal 284. The shocking circuit 282 generates shocking pulses of low (e.g., up to 0.5 joules), moderate (e.g., 0.5-10 joules), or high energy (e.g., 11-40 joules), as selected by the microcontroller 221. Such shocking pulses are applied to the patient's heart 102 through at least two shocking electrodes selected, for example, from the left atrial coil electrode 122, the RV coil electrode 132, and/or the SVC coil electrode 134. As noted above, the case 200 may act as an active electrode in combination with the RV coil electrode 132, or as part of a split electrical vector using the SVC coil electrode 134 or the left atrial coil electrode 122 (i.e., using the RV coil electrode 132 as a common electrode).

Cardioversion shocks are generally considered to be of low to moderate energy level (so as to minimize pain felt by the patient), and/or synchronized with an R-wave and pertain to the treatment of tachycardia. Defibrillation shocks are generally of moderate to high energy level (i.e., corresponding to thresholds in the range of, e.g., 5-40 joules), delivered asynchronously (since R-waves may be too disorganized), and pertain exclusively to the treatment of fibrillation. Accordingly, the microcontroller 221 is capable of controlling the synchronous or asynchronous delivery of the shocking pulses.

More generally, the exemplary stimulation device 100 can be programmed to stimulate different sets of vascular and cardiac muscles through the same lead/electrode system. The exemplary stimulation device 100 can be programmed to vary the output voltage of various pulses to effectively stimulate different muscles of the heart and blood vessels, even though the physical placement of leads and electrodes does not change.

FIG. 3 shows an overview of the exemplary atrial fibrillation therapy engine 238 of FIG. 2. In the illustrated implementation, the atrial fibrillation therapy engine 238 includes an ATP initiation optimizer ("initiation optimizer") 302, a pacing parameters optimizer 304, and an atrial ATP optimizer ("atrial optimizer") 306. The (ATP) initiation optimizer 302 component further includes a multi-chamber analyzer 308, and the atrial (ATP) optimizer 306 component further includes a left atrial (LA) multi-electrode manager 310.

The first component, the initiation optimizer 302, utilizes an observed principle that termination of atrial fibrillation and atrial tachycardia is very often—if not always—associated with at least one indicator of ventricular activation (or sometimes, atrial activation) or a sudden change in such an indicator. Thus, in one implementation, the initiation optimizer 302 looks for a cardiac event favorable for synchronizing ATP to terminate atrial fibrillation. The initation optimizer 302 may looks for a target segment or event of the cardiac cycle as a landmark for initiating ATP. In another implementation, the initiation optimizer 302 looks for sudden changes in a regularly occurring indicator of ventricular activation. Activation is the physical or electrophysiological segment of the cardiac cycle at which a ventricle (or atrium) is electro-stimulated, becomes committed to contract, and/or begins contraction. In the case of ventricular activation, this usually corresponds to the QRS wave morphology. In the case of atrial activation, this usually corresponds to a P wave morphology. The operative principle in the initiation optimizer 302, then, is that indicators of ventricular (or atrial) activation—and sudden changes in these indicators—typically accompany termination of atrial fibrillation or atrial tachycardia and can be used to time the delivery of ATP.

The QRS morphology and axis during atrial arrhythmias is usually the same as that during native heartbeats emanating from the SA node because electrical impulses travel over similar routes, i.e., the AV node, His bundle branch, and Purkinje system. However, a different and/or wider QRS complex can exist during atrial arrhythmias. There may be two reasons for this. The atrial impulse being conducted over usual routes may encounter rate related refractoriness—aberrant conduction—along bundle branches or along the Purkinje fibers, and this may cause bundle branch block and/or fascicular block patterns. This aberrant conduction caused by premature impulses affecting the refractoriness of bundle branches can be understood as physiological and functional. Also, atrial impulses may use auxiliary routes instead of the usual AV node, His bundle, and Purkinje fiber systems to propagate to the ventricles.

One underlying theory or hypothesis that seeks to explain why ventricular activation and associated hemodynamics coincide with termination of atrial fibrillation is that at the moment of termination, the actual walls of one or both of the atria have physically stretched—enough of a stretch perhaps to disrupt geometry of reentrant circuits or to change the conductivity of the myocardial cells. This sudden stretching can be the result of quick pressure changes propagated from a ventricle that is suddenly effectively activated. The effective activation can be caused by the heart's native pulses or by artificially applied pacing. The sudden stretching can also be the result of other hemodynamics that cause a sudden pressure wave or pressure wave reinforcement in one or both of the atria, such as pressure backflow from ventricle to atrium.

Another hypothesis is that ventricular retrograde activation (electrical) travels from ventricle to atrium, fomenting the rhythm. In either case, regardless of which hypothesis best explains coincidence of activation with termination of atrial fibrillation, the initiation optimizer 302 schedules the timing of ATP to a sensed sudden change in atrial or ventricular hemodynamics or activation. This produces increased efficacy in terminating atrial fibrillation using ATP.

Indicators of chamber activation may be subtle or not so subtle. The chemical and physiological events leading up to and occurring during activation are sometimes complex and occur in a split second. Other indicators are fairly obvious, such as the electrical presence of the QRS complex itself, and movement and pressure changes in the heart—the effects of activation. Thus, there are measurable indicators that appear to coincide with termination of atrial fibrillation. The initiation optimizer 302 uses one or more of these indicators to predict when (at which segment of the cardiac cycle) the atrial fibrillation is more likely to be stoppable, and to reinforce the causes of termination (rather than work against them by applying ATP pulses at the wrong time).

The multi-chamber analyzer 308 measures such activation precursors and/or effects. These indicators of ventricular activation, for example, can be electrical, hemodynamic, or mechanical. Thus, to increase the efficacy of ATP for terminating atrial fibrillation of atrial tachycardia, the multi-chamber analyzer 308 carefully monitors parameters associated with ventricular and/or atrial activation to gather input for optimizing the timing of the initiation and/or ongoing delivery of ATP.

The second component of the atrial fibrillation therapy engine 238, the atrial optimizer 306, uses a different schema than the initiation optimizer 302 to optimize the timing of ATP for terminating atrial fibrillation. The atrial optimizer 306 includes the left atrial (LA) multi-electrode manager 310, which was introduced above. The multiple electrodes are disposed around the pulmonary veins that return oxygen rich blood from the lungs to the left atrium. There are specific locations in the vicinity of these pulmonary veins that are more likely than other areas to become atrial fibrillation triggers, i.e., reentrant circuit originators. At each of the multiple left atrium electrodes, the multi-electrode manager 310 senses the cycle duration of reentrant circuits, if any, that may be present and more particularly senses the timing of the excitable gap segment of the reentrant circuit, at each electrode.

The multi-electrode manager 310 also controls the multiple electrodes during delivery of the optimized ATP. The ATP can be delivered in different ways, which will be described in greater detail further below. For example, in one implementation, each pulse of the ATP is delivered in a syncopated manner across the multiple electrodes, so that each ATP pulse is sequentially applied in synchronization with the excitable gap as it passes each electrode in turn.

The pacing parameters optimizer 304 works with either the initiation optimizer 302 or the atrial optimizer 306 to compute the more ancillary pacing parameters to be used during the optimized ATP. That is, once the main timing in each instance is determined, the pacing parameters optimizer 304 optimizes the remaining pacing parameters for maximally terminating atrial fibrillation in the most efficient manner and/or the shortest time. Even though the parameters to be optimized may be considered auxiliary, such as "pacing duration" or "pulse width," the values computed for the parameters are not necessarily conventional, as ATP is conventionally used for other purposes than terminating atrial fibrillation.

Figure 4:
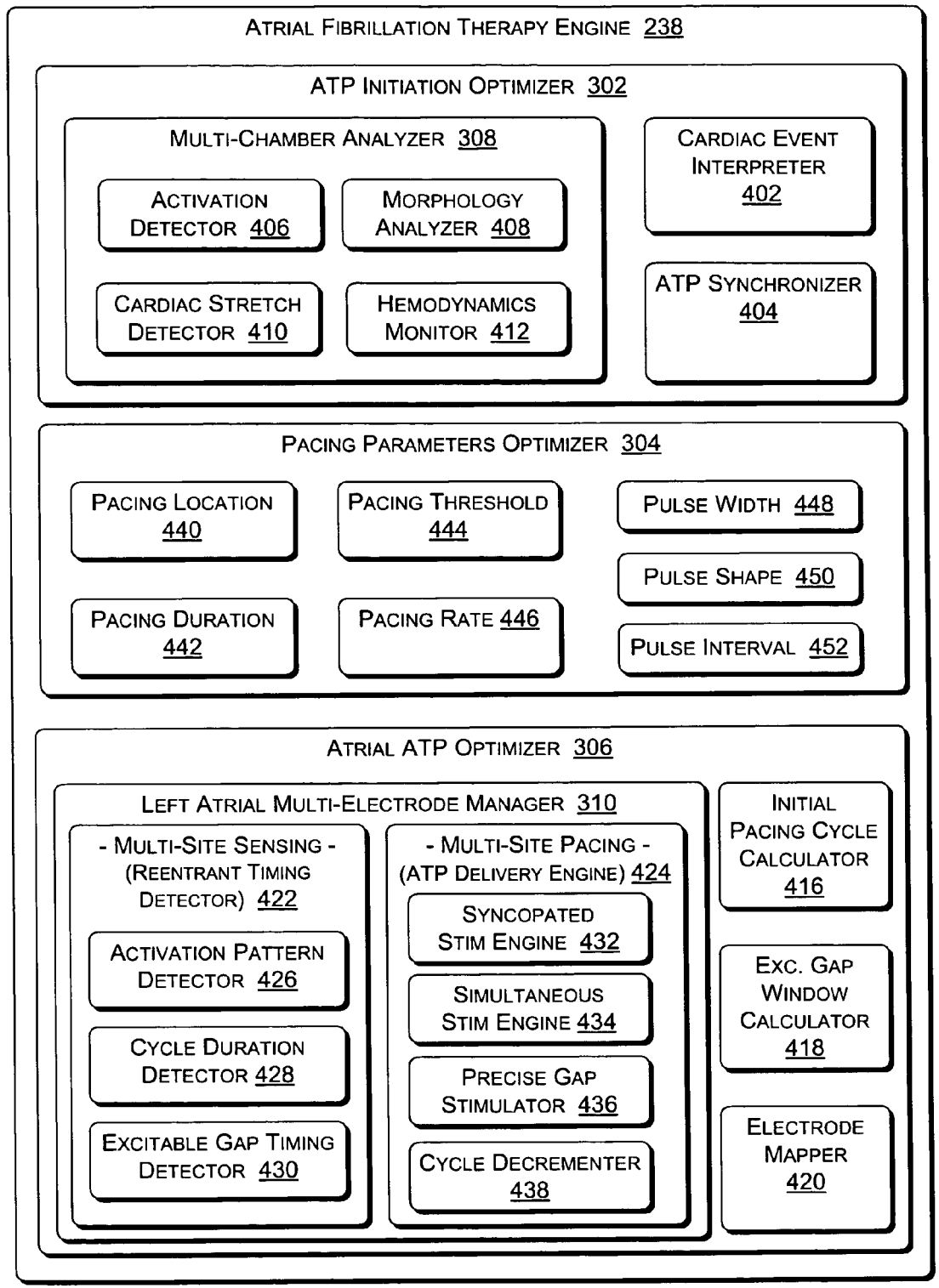
FIG. 4 is a block diagram of the exemplary atrial fibrillation therapy engine of FIG. 3, in greater detail.

FIG. 4 shows the exemplary atrial fibrillation therapy engine 238 of FIGS. 2-3 in greater detail. In this example configuration, the initiation optimizer 302 may include, in addition to the multi-chamber analyzer 308, a cardiac event interpreter 402 and an ATP synchronizer 404. The multi-chamber analyzer 308 may further include an activation detector 406, a morphology analyzer 408, a cardiac stretch detector 410, and a hemodynamics monitor 412.

Likewise, in this example configuration, the atrial optimizer 306 may include, in addition to the left atrial multi-electrode manager 310, an initial pacing cycle calculator 416, an excitable gap window calculator 418, and an electrode mapper 420. The multi-electrode manager 310 may include a multi-site sensing component, such as a reentrant timing detector 422, and complementarily, a multi-site pacing component, such as an ATP delivery engine 424. The reentrant timing detector 422 may further include an activation pattern detector 426, a cycle duration detector 428, and an excitable gap timing detector 430. The ATP delivery engine 424 may further include a syncopated stimulation engine 432, a simultaneous stimulation engine 434, a precise gap stimulator 436, and a cycle decrementer 438.

In this example configuration, the pacing parameters optimizer 304 may include a pacing location optimizer 440, a pacing duration optimizer 442, a pacing threshold optimizer 444, and a pacing rate optimizer 446. The pacing parameters optimizer 304 may also include a pulse width optimizer 448, a pulse shape optimizer 450, and a pulse interval optimizer 452. The pacing parameters optimizer 304 aims to optimize these additional parameters once timing parameters from the ATP initiation optimizer 302 and/or the atrial ATP optimizer 306 are determined. The atrial fibrillation therapy engine 238 then uses all the parameters to deliver ATP in a manner that efficiently terminates atrial fibrillation.

Initiation Optimization

Figure 5:
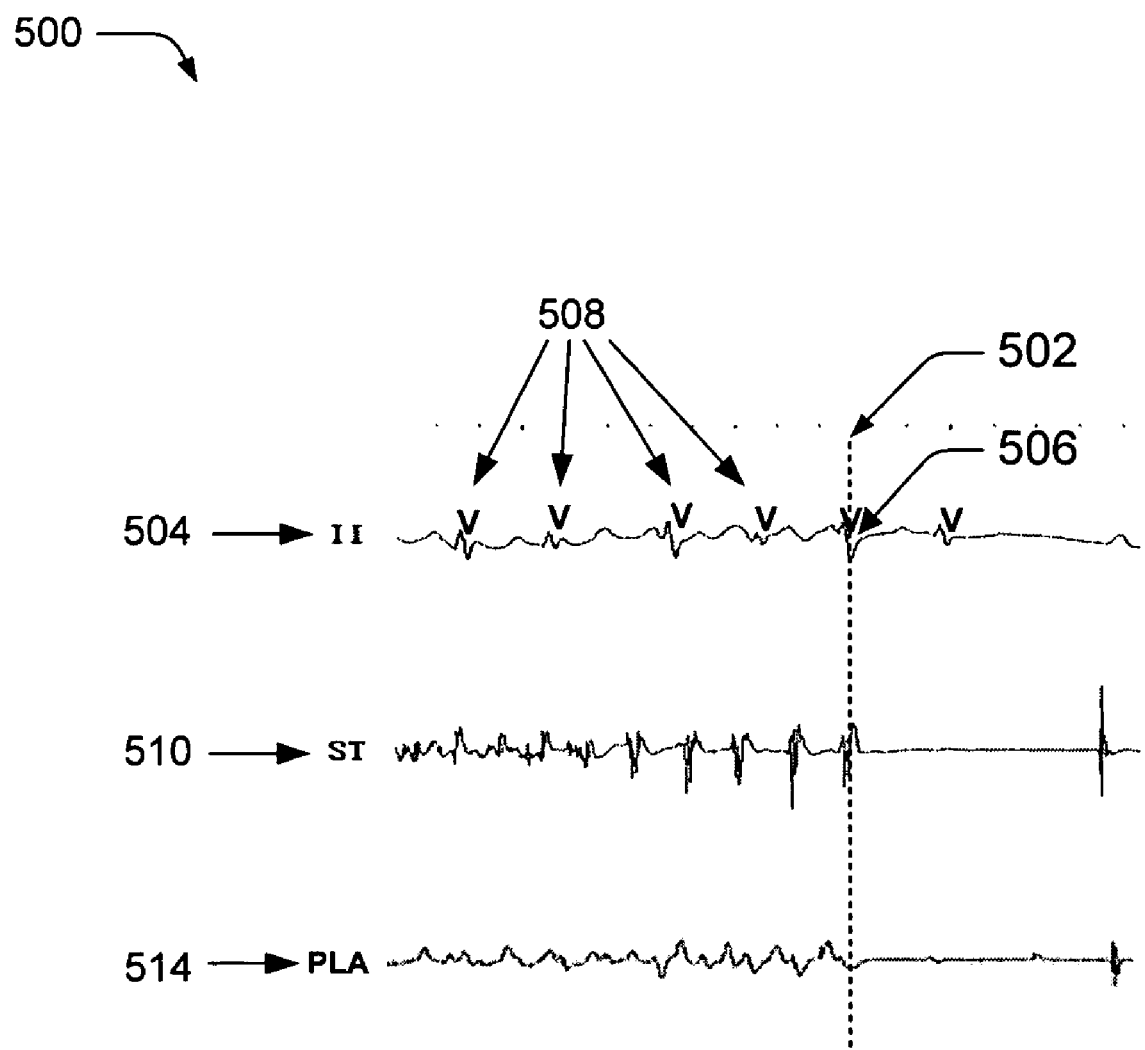
FIG. 5 is a diagram of atrial fibrillation termination coincident with a favorable cardiac event for timing ATP.

With regard to the initiation optimizer 302, FIG. 5 shows an exemplary electrogram 500 recorded during spontaneous termination of atrial fibrillation to illustrate the coincidence of termination with an activation event. The dashed line 502 indicates the moment of termination. At lead II 504 (a surface lead showing body surface potential) a ventricular complex 506 at the dashed line 502 indicates that in this case, ventricular activation is associated with the termination of atrial fibrillation. Other ventricular complexes "V" 508 precede the termination of atrial fibrillation in the illustrated electrogram 500, and thus in future instances of atrial fibrillation, the initiation optimizer 302 can synchronize initiation of ATP with one or more of these ventricular complexes 508. FIG. 5 shows other signals from the atrial epicardial surface. "ST" 510 designates the signal at the sulcus terminalis, an indentation of the myocardial surface of the right atrium, that corresponds to the underlying crista terminalis in which SA node is located.

Figure 6:
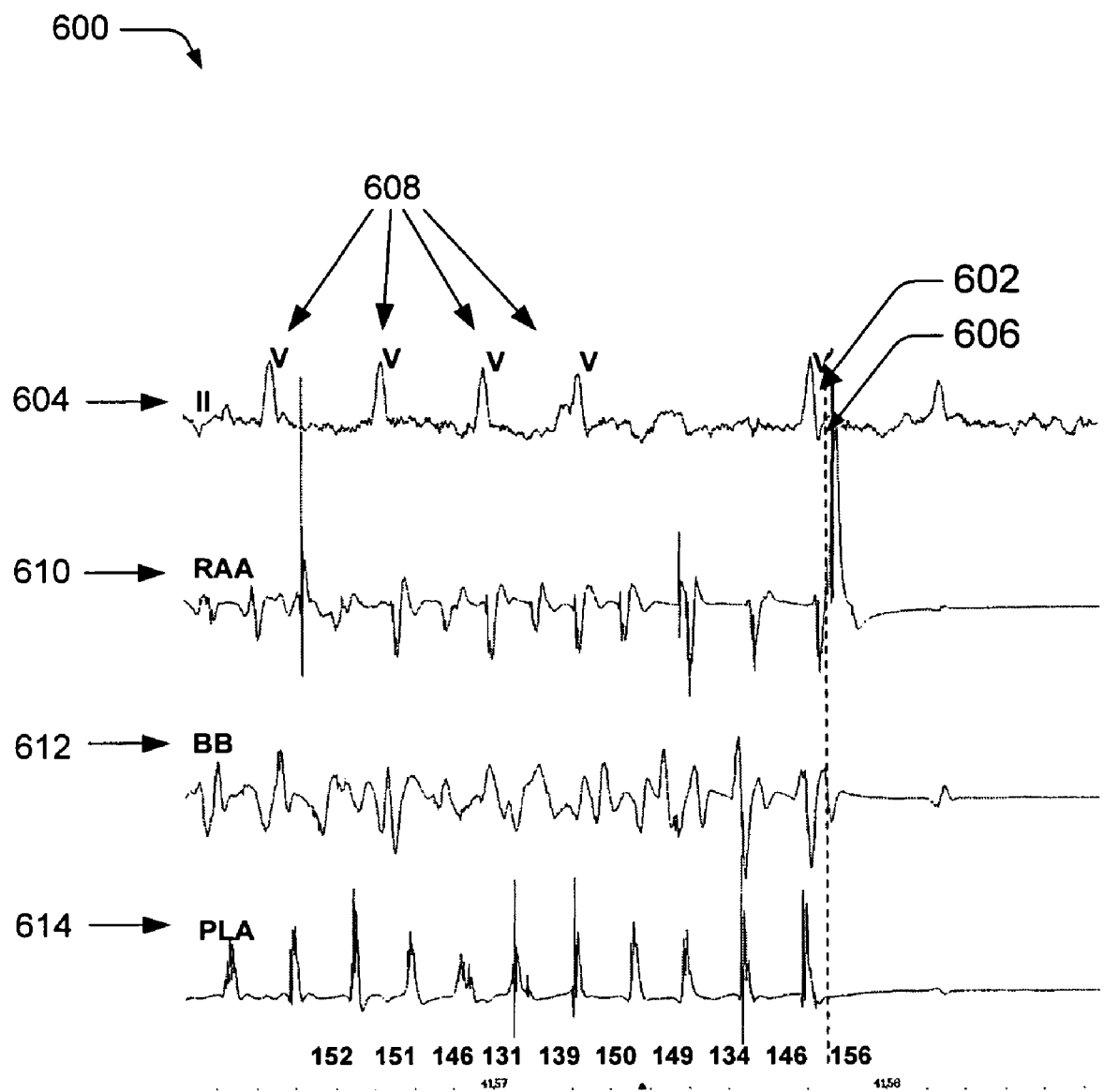
FIG. 6 is a second diagram of atrial fibrillation termination coincident with a favorable cardiac event for timing ATP.

FIG. 6 shows another exemplary electrogram 600 recorded during spontaneous termination of atrial fibrillation to illustrate the coincidence of termination with an activation event. The dashed line 602 again indicates the moment of termination. At lead II 604, a segment of a ventricular complex 606 coincides with the termination of atrial fibrillation. Other ventricular complexes "V" 608 precede the termination of atrial fibrillation in the illustrated electrogram 600. "RAA" 610 designates the signal at the right atrial appendage. "BB" 612 represents the signal at the Bachmann's bundle, which normally conducts the heart's native electrical impulses from the right atrium to left atrium during atrial systole. "PLA" 614 represents the signal at the posterior-inferior left atrium.

Figure 7:
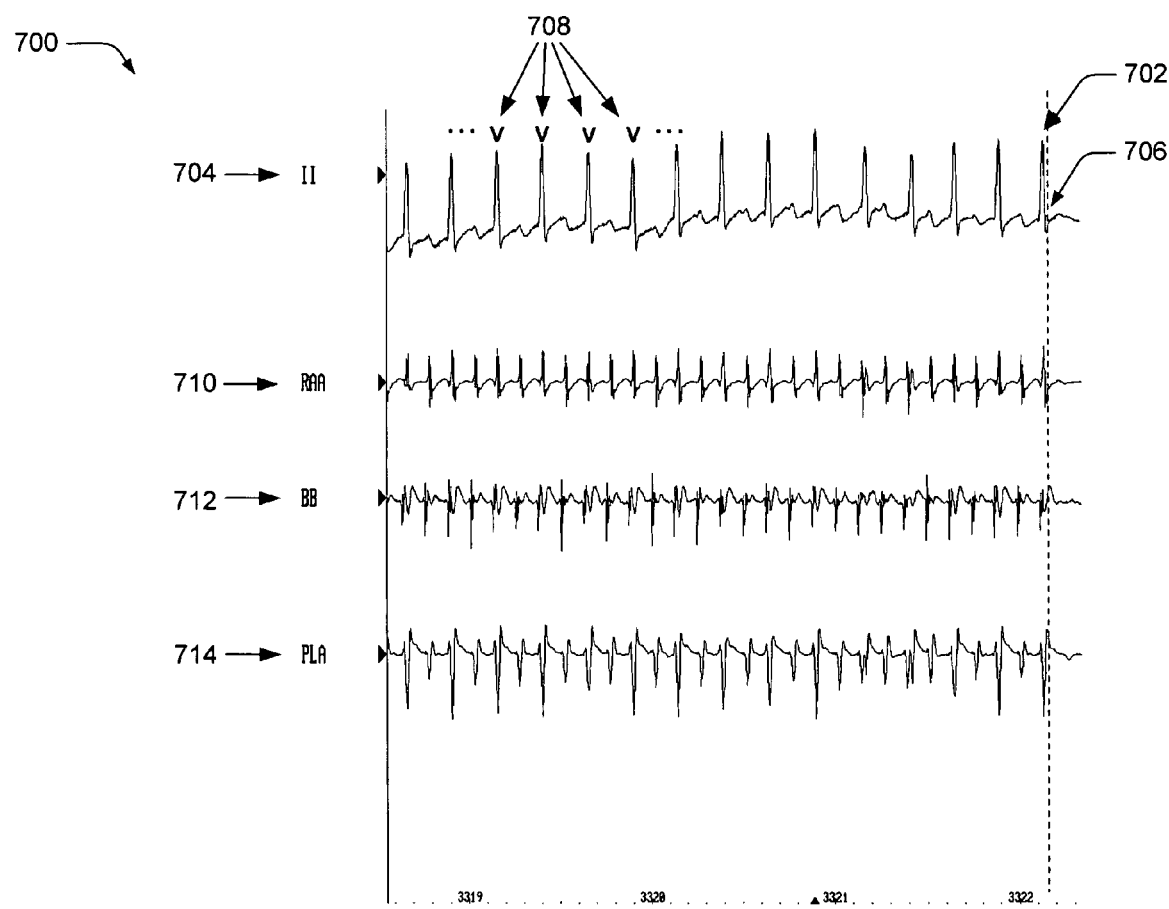
FIG. 7 is a diagram of atrial tachycardia termination coincident with a favorable cardiac event for timing ATP.

FIG. 7 shows another exemplary electrogram 700 recorded during spontaneous termination of atrial tachycardia (in contrast to the above description of termination during atrial fibrillation) to illustrate the coincidence of termination with an activation event. The dashed line 702 again indicates the moment of termination. At lead II 704, a segment of a ventricular complex 706 coincides with the termination of atrial tachycardia. Other ventricular complexes "V" 708 precede the termination of atrial fibrillation in the illustrated electrogram 700. "RAA" 710 designates the signal at the right atrial appendage. "BB" 712 represents the signal at the Bachmann's bundle. "PLA" 714 represents the signal at the posterior-inferior left atrium.

Returning to FIG. 4, the multi-chamber analyzer 308 detects indicators of activation, some of which have been described with respect to FIGS. 5-7, in order to synchronize delivery of ATP with at least one of these indicators.

The initiation optimizer 302 analyzes electrical, mechanical, and/or hemodynamical functioning in the heart chambers. Measurements can include pressure in the chambers, mechanical wall movement of the different regions of the myocardium in the chambers, morphology of electrograms, timing of activation, etc. These parameters are carefully monitored by the multi-chamber analyzer 308 and ATP is timely delivered to the atrium when sudden changes in any of these parameters are noted.

The selection and arrangement of detection components in the illustrated multi-chamber analyzer 308 is just one configuration for the sake of example. Other configurations can also be used. Various sensors can be used to implement the various components, and sensors may overlap in gathering data for more than one of the illustrated components.

The activation detector 406 may utilize the atrial sensing circuits 244 and ventricular sensing circuits 246 available in the exemplary ICD 100 to sense a sudden change in a trending activation parameter. In one implementation, the activation detector 406 senses a retrograde stimulus, that is, an altered electrical stimulus coming back to one of the atria from a respective ventricle (causing a pressure change as well). A retrograde stimulus is sometimes not associated with a sudden change in pressure.

The morphology analyzer 408 can use the morphology detector 236 in the exemplary ICD 100. In one implementation, the morphology analyzer 408 particularly examines the R-wave segment of each cardiac cycle to find a special difference from the R-wave trend. If there is a change in atrial blood pressure at the end of an R-wave, then the cardiac event interpreter 402 may read the change as an initiation point for ATP.

The cardiac stretch detector 410 may sense wall movement vicariously, e.g., via an acute pressure change sensed by the hemodynamics monitor 412. The stretch can also be detected by measuring volume changes, stroke volume, etc. Typically, cardiac stretch can be sensed by monitoring pressure and/or volume changes.

The hemodynamics monitor 412, may use a left-atrial-pressure (LAP) sensor, for example. Various available sensors can be used in combination to detect cardiac stretch, wall movement, pressure change, activation, a particular wave morphology, etc., indicative of a sudden change in activation parameters. For example, a mixed venous blood oxygen saturation ($SvO_2$) sensor in the ventricles and the atria can give hemodynamic values in each chamber. An atrial pressure sensor and the $SvO_2$ sensor can be used in the right atrium to give right atrial hemodynamic functioning. A pressure transducer can be placed in any heart chamber, as can a $SvO_2$ sensor to derive hemodynamics in any chamber. For example, the multi-chamber analyzer 308 can continuously monitor functioning in the ventricles with values derived from these two sensors, and when a change occurs, either positively or negatively, derive a landmark for timing application of ATP.

It should be noted that the initiation optimizer 302 can be adapted to optimize ATP for terminating many kinds of cardiac arrhythmias. The initiation optimizer 302 is not limited to just atrial arrhythmias, but can apply effective ATP therapy to ventricular tachycardias too. Thus, by analyzing both ventricular and atrial functioning, e.g., via the multi-chamber analyzer 308, the initiation optimizer 302 can also optimize timing for ATP therapy for stopping ventricular fibrillation, ventricular tachycardia, etc. The illustrated implementation optimizes by sensing pressure and hemodynamic changes in any heart chamber and then initiating ATP based on a sudden change to initiate the timing of ATP therapy.

In a variation, in which the initiation optimizer 302 also applies therapy for ventricular arrhythmias, the multi-chamber analyzer 308 may at times monitors only the ventricles. For terminating atrial fibrillation, however, the multi-chamber analyzer 308 monitors both atrial and ventricular functioning. Thus, the initiation optimizer 302 as used in the illustrated atrial fibrillation therapy engine 238 monitors trends of hemodynamic parameters in each chamber for an acute change, and delivers ATP in the appropriate atrial chamber using the acute change as a timing landmark.

The cardiac event interpreter 402 sets thresholds for filtering which events (parameter values) detected by the multi-chamber analyzer 308 should trigger initiation of ATP. Thus, the multi-chamber analyzer 308 collects information continuously from, e.g., all four chambers of the heart, and the cardiac event interpreter 402 applies a squelch to this stream of data, so that only a cardiac event that meets the definition of a "sudden change" will initiate ATP for purposes of terminating atrial fibrillation.

The ATP synchronizer 404 receives input from the cardiac event interpreter 402 and commences ATP, e.g., begins ATP when the cardiac event interpreter 402 signals a sudden change in an activation parameter; or, synchronizes initiation of ATP to the sudden change event; or, synchronizes ATP to an anticipated ongoing repetition of the sudden change event.

In one example scenario, the multi-chamber analyzer 308 monitors the four chambers of the heart. The measured venous pressure in the left atrium during an episode of atrial fibrillation is consistently and repeatedly, say, 10 mmHg. Suddenly this pressure rises to 15 mmHg (or drops to 5 mmHg). This sudden change indicates a landmark for initiating ATP to terminate atrial fibrillation. "Initiate" can mean several things. The initiation optimizer 302 can attempt to begin ATP at substantially the same time as—in conjunction with—the detected sudden change. It can also mean concluding that the sudden change coincided with some other cardiac event, and attempting to initiate ATP on the next cyclical occurrence of this same event (e.g., end of ventricular contraction). "Initiation" can even mean attempting to synchronize ongoing ATP with the newly sensed sudden change. In other words, the initiation optimizer 302 monitors trends in the heart chambers, detects an acute change, and times ATP based on the change. In one implementation, a "sudden change" or "acute change" is defined as a sudden 5-10% change in a monitored parameter.

Once the ATP synchronizer 404 has determined a timing for the ATP, the ATP can be applied at a conventional voltage, such as 7-8 volts. The ATP can be delivered via multiple leads, whether applied in one or both atria or in one or both ventricles. The ATP can be applied synchronously or simultaneously over the multiple electrodes, such as the electrodes used by the atrial optimizer 306. Once ATP is triggered by the initiation optimizer 302, the multiple electrodes do not need to sense a condition at each electrode to determine timing, but can just be synchronized to the detected hemodynamic changes or activation. In one implementation, the multiple electrodes can even be placed randomly. Thus, the ATP that is triggered is not limited to treating atrial fibrillation but can also treat ventricular fibrillation, supra ventricular fibrillation, etc.

Atrial Optimizer

The physiological mechanism of atrial fibrillation is often a single, stable, reentrant circuit of very short cycle duration, usually in the pulmonary vein region, which drives the atria, producing fibrillatory conduction. Although ATP is a standard treatment option to terminate most reentrant tachycardias, conventional overdrive pacing techniques to interrupt reentrant tachycardias are virtually always performed by pacing from a single-site on the high right atrium.

Recent studies on ATP for termination of atrial fibrillation have demonstrated disappointing results. The main reason for the disappointment was that the pacing configuration was not optimized (e.g., location, rate, duration, and threshold of pacing). Specifically, ATP has worked satisfactorily for atrial flutter, but since it is attempted on the right side, it has not worked for stopping atrial fibrillation.

In atrial fibrillation, the left side may drive the fibrillation most of the time. A high percentage of patients (e.g., 60-80%) will have a local reentrant circuit started around the pulmonary vein or in some part of the left atrium. Pulmonary veins appear to be more susceptible to this phenomenon, as pulmonary vein features can undergo spontaneous depolarizations called triggered (activity) activation. These triggers, also known as "pumps" may often be responsible for starting the reentrance phenomema—drivers—that lead to sustained atrial fibrillation. If these drivers are eliminated, then the arrhythmias are often eliminated too.

Drivers are typically very regular, and each trigger can initiate many variations of these reentrant pathways. Resulting reentrant circuits can be large or small—i.e., a macro reentrant circuit, or instead, a small micro reentrant circuit, e.g., less then 1 mm in diameter. These small drivers can even mimic a trigger, although they are really small reentrant circuits.

The atrial optimizer 306 provides new pacing techniques to increase the efficacy of atrial fibrillation termination. Multiple unipolar electrodes or multiple pairs of bipolar electrodes are placed on the left atrium both to sense/record and pace. The electrodes to be used to stop atrial fibrillation may be placed epicardially on the left atrium by a sub-xiphoid approach during a pericardial implantation procedure. A hole is made in the pericardium and leads can be connected by daisy-chain or they can independently sense and apply stimuli. The electrode mapper 420 can keep track of the multiple sites. By analyzing atrial activation patterns during atrial fibrillation from electrograms of each electrode site, the atrial optimizer can determine optimal timing parameters and pacing parameters for each of the actual electrode sites in a given patient.

The left atrial multi-electrode manager 310 includes a sensing division 422 and an ATP delivery division 424. The electrode placement sites, even if selected somewhat randomly on the left atrium around the pulmonary vein locations, tend to be within or in proximity to one or more reentrant pathways causing the atrial fibrillation. In one implementation, in a given episode of atrial fibrillation, the electrode mapper 420 identifies which of the multiple electrodes are located within or very close to an active reentrant circuit.

The reentrant timing detector 422 may include components such as the activation pattern detector 426, the cycle duration detector 428, and the excitable gap timing detector 430. These determine, respectively, the presence of a reentrant circuit in relation to electrode sites, the cycle duration of each identified reentrant circuit, and the duration of an excitable gap window that cycles past each electrode that is within or near a reentrant circuit. In one implementation, the atrial optimizer 306 does not count or list a number of reentrant circuits if there is more than one occurring. Instead it records at each electrode the (timing of the) cycling of the excitable gap so that ATP can be synchronized with such windows at each electrode site. In this scenario, it does not matter whether excitable gaps at multiple electrodes are caused by the same reentrant circuit or by multiple reentrant circuits.

The excitable gap window calculator 418 finds a window (i.e., the excitable gap) that can be stimulated to stop atrial fibrillation. In one implementation, the cycle duration detector 428 finds the initial reentrant circuit cycle duration, e.g., by sensing intracellular upstroke potentials, then the window calculator 418 waits 80-90% of cycle, which typically is the starting point of the window. The voltage required can be high, e.g., at a current of 20 mA, 7.5-10 volts may be applied for approximately 0.5 ms.

The cycle duration detector 428 searches for periodic signals at high rates, e.g., 105-107 millisecond cycles (around 10 Hertz), at extremely regular intervals. Unlike regular arrhythmia, these are not typically areas of fibrillatory conduction, but instead are areas, i.e., "sites," where a driver exists. ATP is then applied by the ATP delivery engine 424 to each site, at the cycle duration or frequency. Then, in one implementation, if atrial fibrillation persists, the cycle decrementer 438 calculates a shorter cycle (i.e., a higher frequency) at which to apply ATP in subsequent attempts. For example, subsequent rounds of ATP may be applied at 95%, 90%, 85%, etc., of the initially sensed cycle duration. Relatively large stimuli are used, e.g., up to 100 volts. Thus, if the initial cycle duration is 100 ms or 99 ms, then subsequent bursts of ATP might be given at 95 ms, then 90 ms, then 85 ms, etc., at these regular sites. In one implementation, multiple pulses of ATP are applied five times at each driver site at each cycle duration or frequency. If the atrial fibrillation stops, then the next ATP cycle is not applied. In variations, the cycle duration of the applied ATP is decreased by the cycle decrementer 438 in 5%, 3%, 2%, or 1% intervals. Again, high voltage may be used if the tissue is not very excitable. If there are multiple driver sites, then the syncopated stimulation engine 432 may apply the ATP in sequence so that at each site, the pulse is applied at the cycling window of the excitable gap.

In one implementation, the ATP delivery engine 424 paces simultaneously at multiple sites at a homogenous refractory period. The simultaneous stimulation engine 434 attempts to resynchronize the heart from the spontaneous conduction patterns of atrial fibrillation. By applying ATP at multiple sites at once, this enables resynchronization of the atrium so that refractory periods are homogenized and less likely to have reentrant arrhythmia spontaneously occur. Atrial fibrillation begets atrial fibrillation—atrial fibrillation is more than one mechanism. As refractory periods shrink, the tissue becomes more susceptible to faster reentrant cycles, but if this is controlled by the simultaneous stimulation engine 434 the refractory periods lengthen, and the longer they are, the less likely spontaneous reentry will reoccur, because a larger circuit will be required.

The precise gap stimulator 436 can be used to administer such a simultaneous pulse at all sites at once, delivered at very precise timing during the excitable gap. To successfully capture (i.e., regain control of) the atria during atrial fibrillation, high stimulation amplitude (up to 100 volts) can be used. In one implementation, the precise timing is achieved merely by beginning stimulation timing at the high end of the excitable gap and changing the timing by increments until the low end of the excitable gap is stimulated. Sometime during this range of different timings, the midpoint of the excitable gap is approximated, offering assurance that the excitable gap has been stimulated directly, or "squarely."

In one implementation, when the syncopated stimulation engine 432 applies the ATP, the cycle duration of the applied ATP pulses may be individualized for each electrode site, to coincide with the sensed excitable gap at each site. Thus, while one site may be applying ATP at 10 ms intervals, another electrode may be applying ATP at 92 ms intervals. Application of ATP at each electrode site is synchronized with the cycle duration, as sensed at that site.

In another implementation, the syncopated stimulation engine 432 applies one beat pacing to all electrode sites (every site applies ATP at the same cycle duration) but the beats are applied at different times at each site, because the ATP pulses are synchronized with the excitable gap at each site.

Once optimal timing parameters, appropriate pacing location(s), and other pacing parameters are determined, the ATP delivery engine 424 delivers ATP to one or more of the electrodes to terminate the atrial fibrillation. For example, the excitable gap window calculator 418 determines a window of time—a timing tolerance—in the cycling of a reentrant circuit—during which a pulse of ATP can be delivered at a given electrode to have effect.

Figure 8:
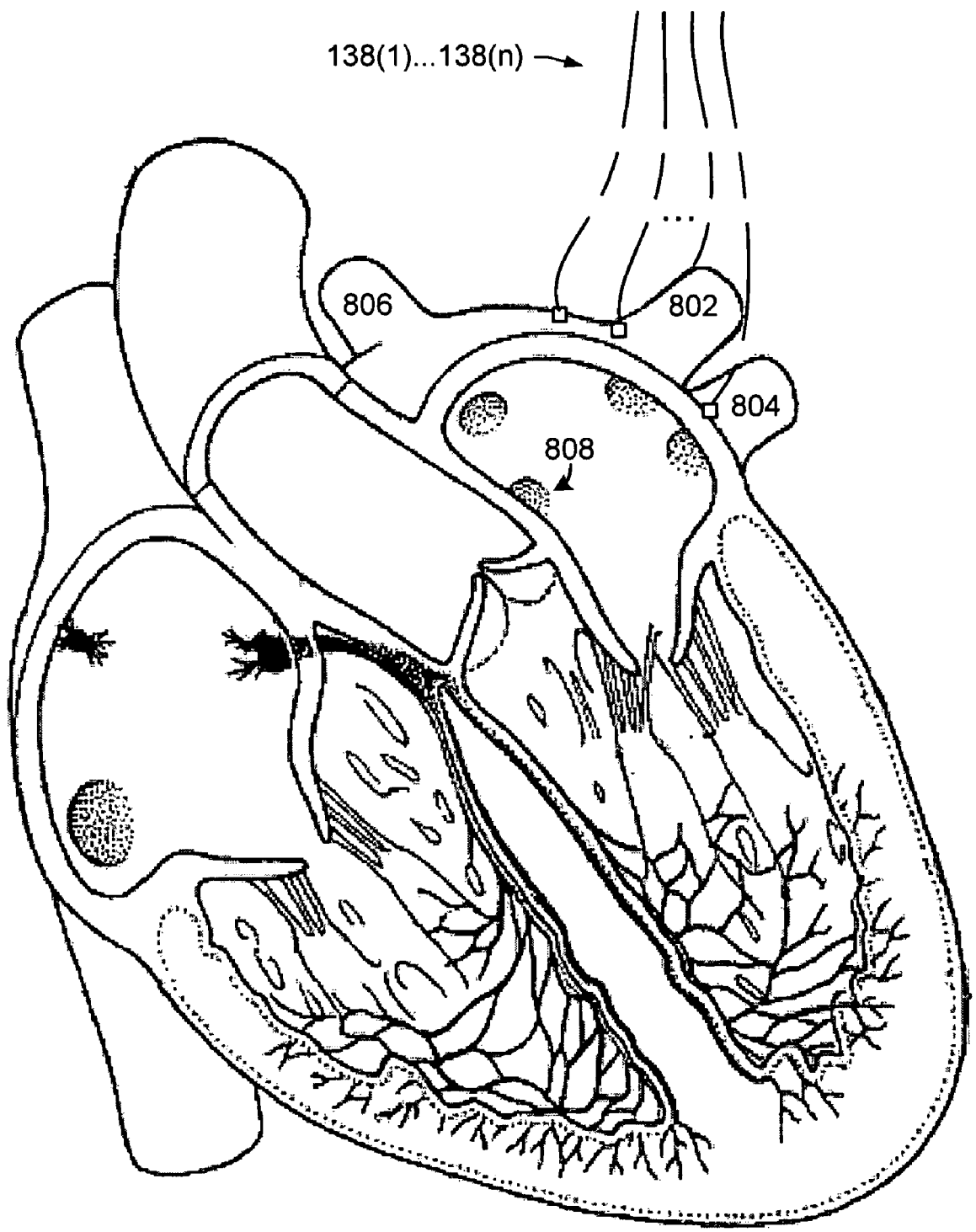
FIG. 8 is a diagram of exemplary electrode placement around the left atrium.
Figure 9:
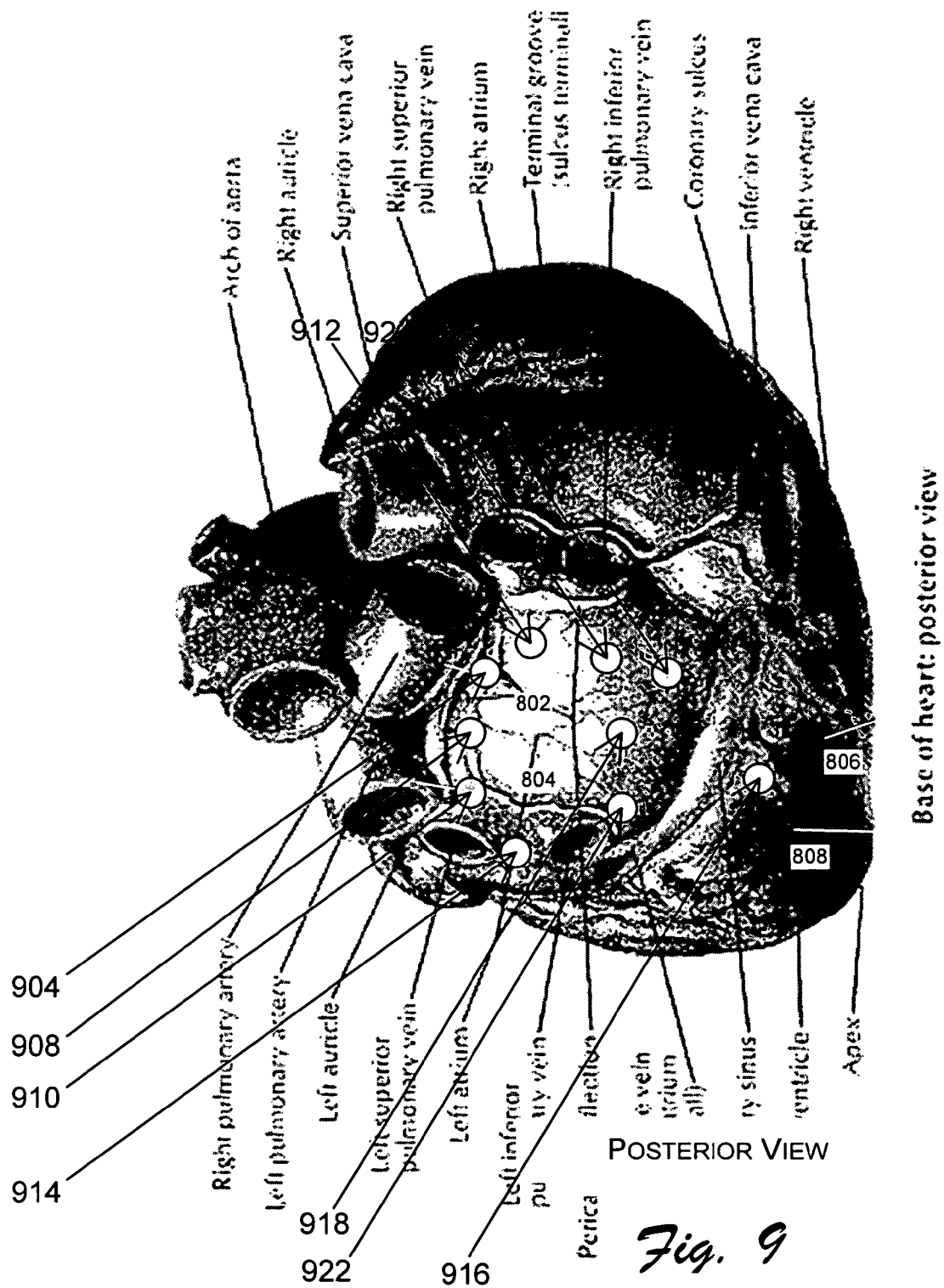
FIG. 9 is another diagram of exemplary electrode placement around the pulmonary veins and Bachmann's bundle of the left atrium

As shown in FIGS. 8 and 9, the multiple electrodes 138(1) ... 138(n) to be controlled by the left atrial multi-electrode manager 310 are placed in significant locations both for sensing reentrant circuits and applying ATP to terminate fibrillatory conduction. FIG. 8 provides an orientation to the relationship of the multiple electrodes 138(1) ... 138(n) with respect to the anatomy of the heart 102. The multiple electrodes 138(1) ... 138(n) can be placed around, between, on, and inside of the pulmonary veins, which return oxygenated blood from the lungs to the heart, to be pumped to the rest of the body. The pulmonary veins connect with the left atrium and include the left superior pulmonary vein 802, the left inferior pulmonary vein 804, the right superior pulmonary vein 806, and the right inferior pulmonary vein 808.

FIG. 9 also shows the epicardial locations of the multiple electrodes 138(1) ... 138(n) strategically placed around the pulmonary veins and in or on the Bachman's Bundle. Exemplary locations are at the junction 904 of the left pulmonary veins (802 and 804) and the left atrial appendage 906; locations (e.g., 908 and 910) lateral to the left pulmonary veins (802 and 804), a location 912 superior to the left superior pulmonary vein 802, and a location 914 inferior to the left inferior pulmonary vein 804. Electrodes can also be placed on the inside surface of the pulmonary veins. Other advantageous locations include a location 916 between the right superior and inferior pulmonary veins (806 and 808), a location 918 between the left and right superior pulmonary veins (802 and 806), a location 920 between the left and right inferior pulmonary veins (804 and 808), and a location 922 in the middle of all pulmonary veins.

Bachmann's bundle is an internodal pathway located in the anterior atria that conducts impulses from the SA node through the atria, eventually to the AV junction, that is, it normally conducts the heart's native electrical impulses from the right atrium to left atrium during atrial systole. It is similar to Wenkeback's pathway, a middle tract, and Thorel's pathway, a posterior tract. Some of the multiple electrodes 138(1) ... 138(n) can also be advantageously places at locations (e.g., 924 and 926) on Bachmann's bundle.

Multiple unipolar electrodes (for example, up to twenty) or multiple pairs (e.g., up to ten) of bipolar electrodes are thus placed epicardially and/or endocardially around the pulmonary veins, inside the pulmonary veins, and Bachmann's bundle. In one scenario, an electroanatomical mapping system (e.g., ENSITE, Endocardial Solutions, Inc., St. Paul, Minn.) may be used for an accurate placement of these multiple electrodes 138(1) ... 138(n) on the epicardial and/or endocardial surfaces.

The multiple electrodes 138(1) ... 138(n) are used for recording/pacing and analyzing the patterns of atrial fibrillation activation in the left atrium. Once atrial fibrillation activation patterns are recognized and analyzed, for example, at each electrode, appropriate pacing is delivered at each electrode site that demonstrates relatively regular and stable atrial activation with minimum variation in cycle duration. Appropriate pacing can mean adequate pacing threshold to activate the atrial tissue, starting at an initial pacing cycle duration of the driving reentrant circuit, for example, and then applying groups of pulses. The cycle decrementer 438 decreases the pacing cycle duration in given decrements, e.g., two millisecond decrements, between groups of pulses. The decrementing can continue until approximately 40 milliseconds have been subtracted as compared with the cycle duration of the driving reentrant circuit driving the atrial fibrillation.

In one implementation, the ATP is applied one electrode at a time, beginning at the electrode that demonstrates the highest regular and stable atrial activation with minimum variation in cycle duration. If ATP applied at this electrode fails to terminate the atrial fibrillation, then the multi-electrode manager 310 progresses to the electrode with the next highest regular and stable atrial activation with minimum variation in cycle duration, and so on.

In another implementation, the atrial optimizer 306 and the pacing parameters optimizer 304 calculate the timing and other pulse characteristic and delivery parameters, and then the syncopated stimulation engine 432 applies each pulse of the ATP in a syncopated manner across the multiple electrodes, so that each ATP pulse is sequentially applied in synchronization with the excitable gap as it passes each electrode in turn.

Even if the syncopated application of ATP just described fails to end the atrial fibrillation, then as a next option the simultaneous stimulation engine 434 applies ATP simultaneously at multiple selected sites or at all the available sites, perhaps as a last option for ATP treatment of atrial fibrillation.

Figure 12:
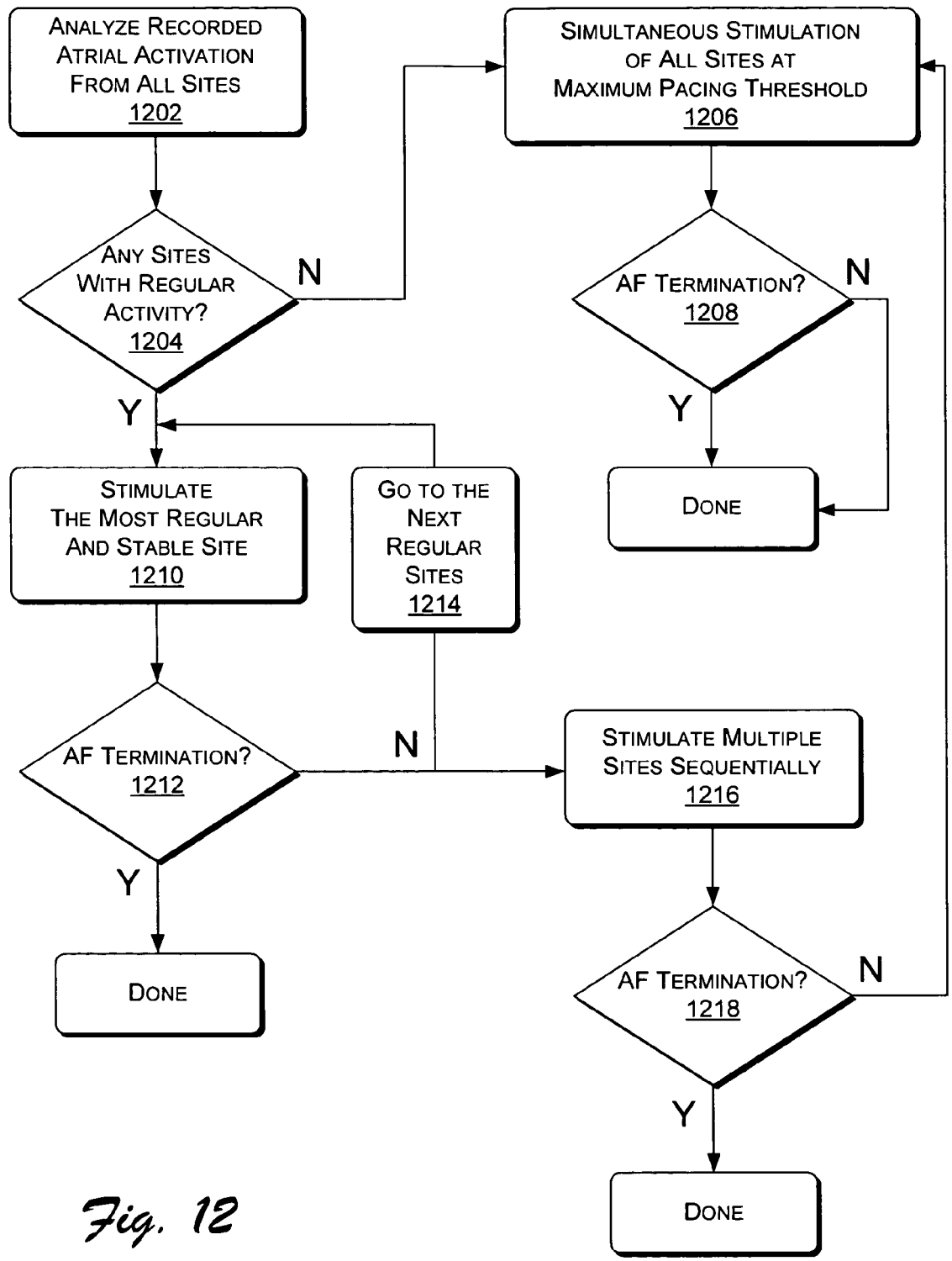
FIG. 12 is a flow diagram of a third exemplary method of treating atrial fibrillation using ATP.

Thus, the atrial optimizer 306 can apply a hierarchical protocol of increasingly invasive ATP applications. FIG. 12, to be described below, shows a pacing protocol that combines some of these various implementations.

Pacing Parameters Optimizer

For either the initiation optimizer 302 or the atrial optimizer 306, the pacing parameters optimizer 304 can determine the number of the pacing stimuli to apply, the pulse width, the various time intervals between the pacing stimuli, etc. The pacing location optimizer 440 may include default electrode sites and configurations in case the initiation optimizer 302 or the atrial optimizer 306 do not specify initial starting sites for applying the ATP. Typically, the pacing duration optimizer 442, the pacing threshold optimizer 444, the pacing rate optimizer 446; as well as the pulse width optimizer 448, the pulse shape optimizer 450, and the pulse interval optimizer 452 optimize ATP parameters to minimize discomfort to patients, power consumption of the device, and also to reduce proarrhythmic effects of pacing. Thus, the optimal number of stimuli and typically a relatively lower pacing threshold will be selected as a part of the optimization process.

Exemplary Methods

FIG. 10 shows an exemplary method 1000 of terminating atrial fibrillation using optimized ATP. The exemplary method 1000 may be implemented in connection with many suitably configured stimulation devices, although it will be described as being executed by the exemplary atrial fibrillation therapy engine 238 of the exemplary stimulation device 100. In the flow diagram of FIG. 10, the operations are summarized in individual blocks. Some operations may be performed in hardware and/or as machine-readable instructions (software or firmware) that can be executed by a processor, such as microcontroller 221.

At block 1002, the left atrium of the heart can paced and sensed by multiple electrodes electrically connected to the left atrium. In order to place multiple electrodes epicardially in target areas around the pulmonary veins, and Bachmann's bundle, etc., the pericardial sac may be entered via a sub-xiphoid approach and the electrodes mapped to sites where drivers for sustaining atrial fibrillation likely originate. Placing multiple electrodes epicardially on the left atrium does not preclude having electrodes located on the endocardiac surfaces of the left atrium or inside the pulmonary veins.

At block 1004, reentrant circuits (or sometimes their triggers) are sensed. Using the multiple electrodes implanted on the left atrium, each electrode becomes a site for listening for the regular, relatively high frequency cycling of a reentrant circuit, or the fibrillatory conduction being propagated from such a circuit. If only one reentrant circuit is active, then each electrode may sense a slightly different amplitude of the cyclical conduction and at a slightly different time, depending on distance of a particular electrode from the physical position of the reentrant circuit. If more than one reentrant circuit is active, then different electrodes may sense different frequencies and amplitudes of cycling.

At block 1006, ATP is delivered at one or more of the multiple sites. In one implementation, ATP that is timed to the same frequency as a reentrant circuit is applied at multiple electrodes on the left atrium, but each pulse is applied in a syncopated manner across electrodes, that is, at a different time at each electrode to coincide with an apparent presence or proximity of the excitable gap part of the reentrant circuit at each electrode.

In another implementation, the ATP may be applied at a different frequency at each electrode if there are multiple reentrant circuits being sensed by different electrodes at different frequencies.

In yet another implementation, ATP is only applied at one electrode at a time, beginning with the electrode that senses the most stable and regular reentrant circuit. If atrial fibrillation still persists, then the ATP is applied at the electrode that senses the second-most stable and regular reentrant circuit, and so on.

In yet another implementation, the ATP is applied strictly simultaneously at all available electrodes on the left atrium in an attempt to resynchronize the electrical conduction of the atrium. In this case, the frequency of the applied ATP may be different from the frequency of an active reentrant circuit in order to override the arrhythmia.

In many of these implementations just described, the frequency of the applied ATP may be increased in stepped increments, if atrial fibrillation persists. In one implementation, for example, five groups of five pulses are applied at the frequency of the reentrant circuit, and if atrial fibrillation persists, then the frequency is increased by 2% or 5% increments, for example, for each succeeding application of the pattern.

Figure 11:
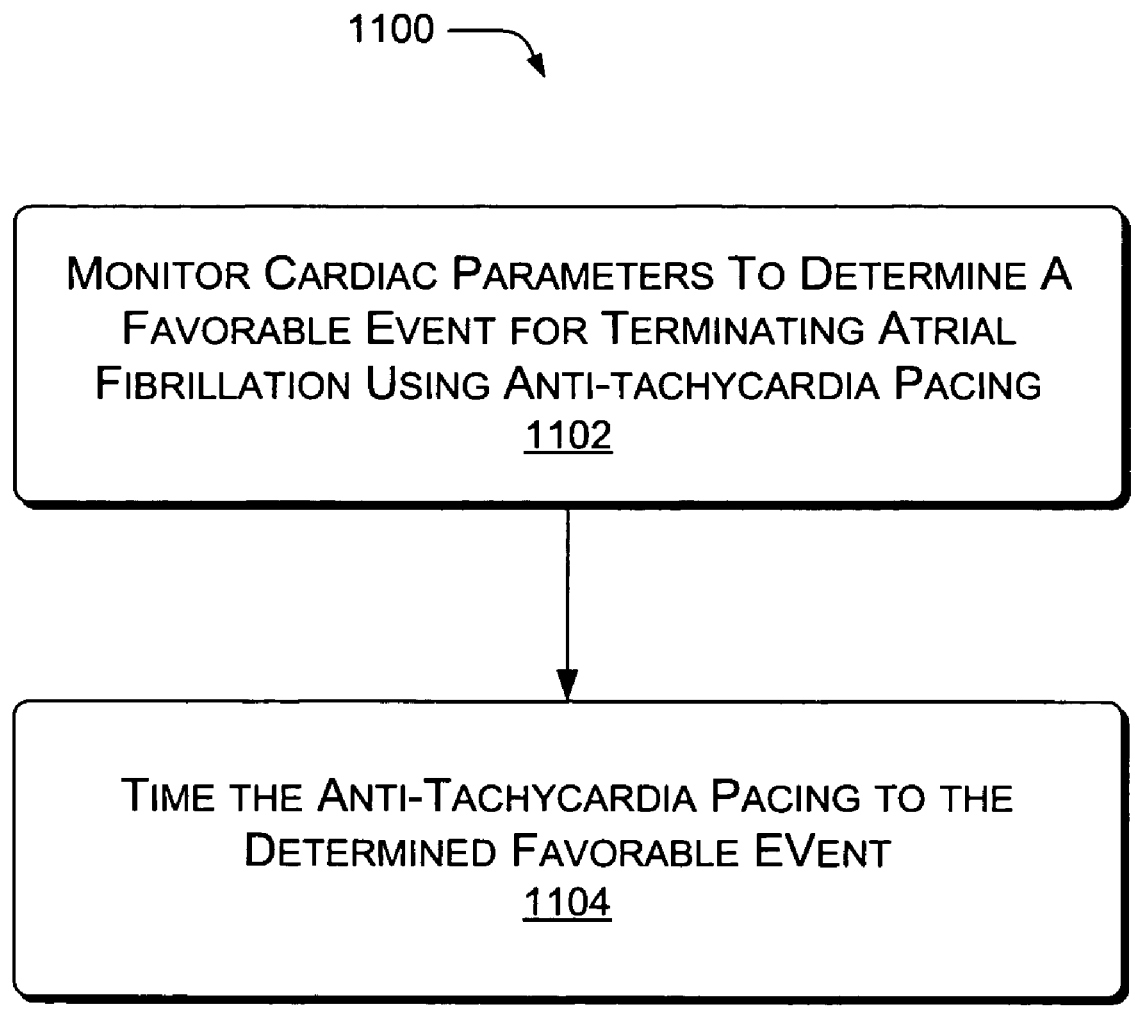
FIG. 11 is a flow diagram of a second exemplary method of treating atrial fibrillation using ATP.

FIG. 11 shows another exemplary method 1100 of terminating atrial fibrillation using optimized ATP. The exemplary method 1100 may be implemented in connection with many suitably configured stimulation devices, although it will be described as being executed by the exemplary atrial fibrillation therapy engine 238 of the exemplary stimulation device 100. In the flow diagram of FIG. 11, the operations are summarized in individual blocks. Some operations may be performed in hardware and/or as machine-readable instructions (software or firmware) that can be executed by a processor, such as microcontroller 221.

At block 1102, cardiac parameters are monitored in order to find a favorable event for terminating atrial fibrillation via ATP. When ATP is synchronized with or timed to such a favorable event, the chances of the ATP terminating atrial fibrillation are increased, hence the ATP is optimized. Such favorable cardiac events include, for example, segments of the QRS complex of the cardiac cycle, which often coincide with termination of atrial fibrillation in a natural setting—i.e., without external intervention. Other favorable events with which to synchronize ATP for purposes of terminating atrial fibrillation include: a sudden change in a morphology of an electrical waveform of a cardiac cycle, particularly the morphology near the end of ventricular conduction leading to contraction (i.e., near QRS or T waves); a sudden change in a hemodynamic parameter (e.g., cardiac output, or an intracardiac pressure); or a relatively pronounced mechanical movement of a wall of the heart.

At block 1104, the ATP is timed to the favorable event. In some implementations, an implanted device tries to time a first pulse of ATP to the event itself (e.g., within milliseconds) to reinforce the favorable event, if the device has a fast enough response time. In other implementations, the ATP is synchronized to points on succeeding cardiac cycles corresponding to the first detection of the favorable event.

FIG. 12 shows another exemplary method 1200 of terminating atrial fibrillation using optimized ATP. The method 1200 can be used as a pacing protocol for termination atrial fibrillation. At each pacing stage, the pacing parameters can be optimized. The exemplary method 1200 may be implemented in connection with many suitably configured stimulation devices, although it will be described as being executed by the exemplary atrial fibrillation therapy engine 238 of the exemplary stimulation device 100. In the flow diagram of FIG. 12, the operations are summarized in individual blocks. Some operations may be performed in hardware and/or as machine-readable instructions (software or firmware) that can be executed by a processor, such as microcontroller 221.

At block 1202, atrial activation is analyzed from each of multiple electrode sites on the left atrium.

At block 1204, each site is analyzed for regular activation activity, that is, the presence of a reentrant circuit, or fibrillatory conduction propagating from a reentrant circuit.

At block 1206, if there are no sites with regular activity, then all sites are stimulated at once at the maximum pacing threshold. This stimulation attempts to resynchronize the electrical conduction of the atrium At block 1208, a determination is made of whether atrial fibrillation has been terminated.

At block 1210, if one or more sites were found at block 1204 that sensed regular activity, then the site that sensed the most stable and regular activity is stimulated first, for example, with ATP tuned to the frequency of the cycle duration of the stable and regular activity.

At block 1212, a check is then made to see if atrial fibrillation has terminated.

At block 1214, if the atrial fibrillation has not yet terminated, then the site that sensed the second-most stable and regular activity is stimulated next, and so on, through the various electrode sites, if the atrial fibrillation persists.

At block 1216, if the atrial fibrillation still persists, then syncopated stimulation is applied at the multiple sites, that is, each pulse of ATP is applied at a site when the excitable gap of a reentrant circuit passes under or near the electrode at that site.

At block 1218, a determination is made whether atrial fibrillation has been terminated. If not, then in one implementation, the method 1200 applies ATP to all sites at once at maximum pacing threshold, as at block 1206.

CONCLUSION

Although exemplary systems and methods have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

What is claimed is:

1. An implantable device, comprising:
control circuitry configured to control multiple electrodes wherein each electrode of the multiple electrodes is configured for placement at an epicardial position adjacent a left atrium of a heart, an endocardial position adjacent a left atrium of a heart, an intravenous position adjacent a left atrium of a heart, or a position in contact with a pulmonary vein;
a cycle detector configured to sense a cycle duration frequency of a repeating reentrant circuit causing atrial fibrillation in the heart based at least in part on electrical signals of the heart sensed via one or more of the multiple electrodes;
a timing detector configured to sense a timing at each of the multiple electrodes of a repeating excitable gap of the repeating reentrant circuit;
anti-tachycardia pacing (ATP) delivery circuitry configured to apply ATP pulses at one or more of the multiple electrodes, based at least in part on a cycle duration sensed by the cycle detector and timings sensed by the timing detector, to terminate the atrial fibrillation;
wherein the ATP delivery circuitry comprises circuitry configured to apply each pulse of the ATP at a different time at each electrode, of the one or more electrodes, according to a frequency associated with the cycle duration of the repeating reentrant circuit wherein the ATP pulse time at each electrode, of the one or more electrodes, is synchronized to coincide with the excitable gap being present at the electrode; and
wherein the ATP delivery circuitry comprises circuitry configured to:
determine a regularity of the repeating excitable gap sensed at each of the multiple electrodes;
rank the multiple electrodes according to the regularity;
apply the ATP at one of the multiple electrodes, the one having the highest regularity rank; and
if the atrial fibrillation persists, to apply the ATP at each of the other multiple electrodes in turn, according to their regularity rank.

2. The implantable device as recited in claim 1, further comprising a cycle decrementer configured to increase frequency of ATP pulses applied at the one or more electrodes if the atrial fibrillation persists.

3. The implantable device as recited in claim 1, wherein, if the cycle detector detects multiple different reentrant circuits, the frequency of ATP being applied at each electrode, of the one or more electrodes, is associated with a cycle duration of a corresponding one of the multiple different reentrant circuits; and
wherein the ATP pulse time at each electrode, of the one or more electrodes, is synchronized to coincide with the excitable gap of a corresponding one of the reentrant circuits being present at the electrode.

4. The implantable device as recited in claim 1, further comprising a simultaneous stimulation circuitry configured to apply additional ATP pulses at each of two or more of the multiple electrodes simultaneously to resynchronize electrical conduction in the left atrium.

5. The implantable device as recited in claim 1, further comprising precise gap stimulator circuitry configured to apply additional ATP pulses simultaneously at two or more of the multiple electrodes during different parts of the excitable gap over multiple cycles of the excitable gap.

6. The implantable device as recited in claim 1, wherein the ATP delivery circuitry comprises circuitry configured to apply ATP to the one or more electrodes at a voltage between approximately 8.5 volts and approximately 100 volts.

7. The implantable device as recited in claim 1, further comprising circuitry configured to determine if regularity exists for the repeating excitable gap at any one of the multiple electrodes and, responsive to a lack of regularity at any one of the multiple electrodes, to call for delivery of ATP pulses simultaneously at two or more of the multiple electrodes.

8. The implantable device as recited in claim 7, wherein the call for delivery of ATP pulses simultaneously calls for delivery of ATP pulses at a maximum pacing threshold.

* * * * *